(12) United States Patent
Dube et al.

(10) Patent No.: US 10,499,684 B2
(45) Date of Patent: Dec. 10, 2019

(54) TOBACCO-DERIVED FLAVORANTS

(71) Applicant: R.J. Reynolds Tobacco Company, Winston-Salem, NC (US)

(72) Inventors: Michael Francis Dube, Winston-Salem, NC (US); William Monroe Coleman, III, Winston-Salem, NC (US); Chelsea Allison Cooke, Winston-Salem, NC (US); Courtney Guenther Culbert, Pfafftown, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 221 days.

(21) Appl. No.: 15/009,199

(22) Filed: Jan. 28, 2016

(65) Prior Publication Data
US 2017/0215472 A1   Aug. 3, 2017

(51) Int. Cl.
*A24B 15/28* (2006.01)
*A24B 15/24* (2006.01)
(Continued)

(52) U.S. Cl.
CPC ............ *A24B 15/38* (2013.01); *A24B 15/241* (2013.01); *A24B 15/28* (2013.01); *A24B 15/306* (2013.01); *A24B 15/307* (2013.01); *A24D 1/002* (2013.01); *C07D 241/12* (2013.01); *C12P 19/02* (2013.01); *C12P 19/14* (2013.01); *C12P 19/24* (2013.01); *C13K 1/04* (2013.01); *C25B 1/16* (2013.01)

(58) Field of Classification Search
CPC ............................ A24B 15/38; A24B 15/241
USPC ........................................................ 131/278
See application file for complete search history.

(56) References Cited

U.S. PATENT DOCUMENTS 1,358,302 A * 11/1920 Ellwood .................. D21B 1/06
                                                                172/39
1,376,586 A    5/1921 Schwartz
(Continued)

FOREIGN PATENT DOCUMENTS

CN    1133694    10/1996
CN    1324586    12/2001
(Continued)

OTHER PUBLICATIONS

William A. O'Deen and Lynn K. Porter, "Devarda's Alloy Reduction of Nitrate and Tube Diffusion of the Reduced Nitrogen for Indophenol Ammonium and Nitrogen-15 Determinations". Analytical Chemistry, 52, 1164-1166, 1980.*

(Continued)

*Primary Examiner* — Eric Yaary
*Assistant Examiner* — Russell E Sparks
(74) *Attorney, Agent, or Firm* — Womble Bond Dickinson (US) LLP

(57) ABSTRACT

Methods of forming pyrazines from reactants derived from a plant of the *Nicotiana* species, including receiving an aqueous reactant solution including at least one tobacco-derived cellulosic sugar and at least one tobacco-derived amino acid, heating the reactant solution to a reactant temperature and holding the reactant solution at the reactant temperature for a reactant time to produce a reactant product including at least one tobacco-derived pyrazine, and isolating the at least one tobacco-derived pyrazine from the reactant product. Tobacco products incorporating the tobacco-derived pyrazines are also provided.

20 Claims, 11 Drawing Sheets

(51) Int. Cl.

|  |  |
|---|---|
| *C07D 241/12* | (2006.01) |
| *C12P 19/02* | (2006.01) |
| *C25B 1/16* | (2006.01) |
| *A24B 15/38* | (2006.01) |
| *A24D 1/00* | (2006.01) |
| *C12P 19/14* | (2006.01) |
| *C12P 19/24* | (2006.01) |
| *C13K 1/04* | (2006.01) |
| *A24B 15/30* | (2006.01) |

(56) References Cited

U.S. PATENT DOCUMENTS

| | | | |
|---|---|---|---|
| 1,915,428 | A * | 6/1933 | Lambert .......... C01D 9/14 23/297 |
| 2,766,148 | A | 10/1956 | Rowland |
| 2,774,680 | A | 12/1956 | Hackney et al. |
| 3,424,171 | A | 1/1969 | Rooker |
| 3,616,221 | A * | 10/1971 | Takasaki .......... C12N 9/92 435/234 |
| 3,696,917 | A | 10/1972 | Levi |
| 4,008,210 | A | 2/1977 | Steele et al. |
| 4,009,290 | A | 2/1977 | Okumori et al. |
| 4,045,879 | A | 9/1977 | Witte |
| 4,056,442 | A | 11/1977 | Huang et al. |
| 4,069,828 | A | 1/1978 | Hall et al. |
| 4,122,104 | A | 10/1978 | Witte |
| 4,131,118 | A * | 12/1978 | Gellatly .......... A24B 15/24 131/297 |
| 4,144,895 | A | 3/1979 | Fiore |
| 4,150,677 | A | 4/1979 | Osborne, Jr. et al. |
| 4,244,381 | A | 1/1981 | Lendvay |
| 4,251,671 | A | 2/1981 | Alter et al. |
| 4,253,929 | A * | 3/1981 | Keritsis .......... B01D 61/44 131/297 |
| 4,267,847 | A | 5/1981 | Reid |
| 4,268,632 | A | 5/1981 | Wildman et al. |
| 4,289,147 | A | 9/1981 | Wildman et al. |
| 4,298,013 | A * | 11/1981 | Semp .......... A24B 15/20 131/308 |
| 4,298,540 | A | 11/1981 | Youn et al. |
| 4,308,877 | A | 1/1982 | Mattina |
| 4,322,569 | A | 3/1982 | Chao et al. |
| 4,334,095 | A | 6/1982 | Baniel |
| 4,340,676 | A | 7/1982 | Bourque |
| 4,347,324 | A | 8/1982 | Wildman et al. |
| 4,351,346 | A | 9/1982 | Brummer et al. |
| 4,359,059 | A | 11/1982 | Brummer et al. |
| 4,359,417 | A | 11/1982 | Karnofsky et al. |
| 4,381,407 | A | 4/1983 | Bremus et al. |
| 4,400,471 | A | 8/1983 | Johal |
| 4,456,556 | A | 6/1984 | Grimsby |
| 4,456,557 | A | 6/1984 | Grimsby |
| 4,466,923 | A | 8/1984 | Friedrich |
| 4,476,881 | A | 10/1984 | Gravely et al. |
| 4,506,682 | A | 3/1985 | Muller |
| 4,513,756 | A | 4/1985 | Pittman et al. |
| 4,515,726 | A | 5/1985 | Sullivan |
| 4,528,993 | A | 7/1985 | Sensabaugh, Jr. et al. |
| 4,588,691 | A | 5/1986 | Johal |
| 4,589,428 | A | 5/1986 | Keritsis |
| 4,605,016 | A | 8/1986 | Soga et al. |
| 4,607,479 | A | 8/1986 | Linden |
| 4,612,942 | A | 9/1986 | Dobberstein et al. |
| 4,622,982 | A | 11/1986 | Gaisch et al. |
| 4,624,269 | A | 11/1986 | Story et al. |
| 4,631,899 | A | 12/1986 | Nielsen |
| 4,716,911 | A | 1/1988 | Poulose et al. |
| 4,727,889 | A | 3/1988 | Niven, Jr. et al. |
| 4,847,106 | A | 7/1989 | Pike et al. |
| 4,887,618 | A | 12/1989 | Bernasek et al. |
| 4,895,175 | A | 1/1990 | Baskevitch et al. |
| 4,941,484 | A | 7/1990 | Clapp et al. |
| 4,967,771 | A | 11/1990 | Fagg et al. |
| 4,967,773 | A | 11/1990 | Shaw |
| 4,986,286 | A | 1/1991 | Roberts et al. |
| 4,987,907 | A | 1/1991 | Townend |
| 4,991,599 | A | 2/1991 | Tibbetts |
| 5,005,593 | A | 4/1991 | Fagg |
| 5,018,540 | A | 5/1991 | Grubbs et al. |
| 5,060,669 | A | 10/1991 | White et al. |
| 5,065,775 | A | 11/1991 | Fagg |
| 5,074,319 | A | 12/1991 | White et al. |
| 5,077,071 | A | 12/1991 | Strop |
| 5,092,352 | A | 3/1992 | Sprinkle, III et al. |
| 5,099,862 | A | 3/1992 | White et al. |
| 5,110,605 | A | 5/1992 | Acharya |
| 5,121,757 | A | 6/1992 | White et al. |
| 5,131,415 | A | 7/1992 | Munoz et al. |
| 5,143,097 | A | 9/1992 | Stephen Sohn et al. |
| 5,148,819 | A | 9/1992 | Fagg |
| 5,159,942 | A | 11/1992 | Brinkley et al. |
| 5,167,244 | A | 12/1992 | Kjerstad |
| 5,197,494 | A | 3/1993 | Kramer |
| 5,230,354 | A | 7/1993 | Smith et al. |
| 5,234,008 | A | 8/1993 | Fagg |
| 5,235,992 | A | 8/1993 | Sensabaugh, Jr. |
| 5,243,999 | A | 9/1993 | Smith |
| 5,296,621 | A | 3/1994 | Roos et al. |
| 5,301,694 | A | 4/1994 | Raymond et al. |
| 5,318,050 | A | 6/1994 | Gonzalez-Parra et al. |
| 5,343,879 | A | 9/1994 | Teague |
| 5,346,734 | A | 9/1994 | Wydick, Jr. |
| 5,360,022 | A | 11/1994 | Newton et al. |
| 5,387,416 | A | 2/1995 | White et al. |
| 5,397,571 | A | 3/1995 | Roland et al. |
| 5,426,220 | A | 6/1995 | Baniel et al. |
| 5,435,325 | A | 7/1995 | Clapp et al. |
| 5,445,169 | A | 8/1995 | Brinkley et al. |
| 5,533,530 | A | 7/1996 | Young et al. |
| 5,715,844 | A | 2/1998 | Young et al. |
| 5,724,998 | A | 3/1998 | Gellatly et al. |
| 5,733,574 | A | 3/1998 | Dam |
| 5,859,263 | A | 1/1999 | Ghorpade et al. |
| 5,932,095 | A | 8/1999 | Walters et al. |
| 6,033,895 | A | 3/2000 | Garger et al. |
| 6,083,729 | A | 7/2000 | Martin et al. |
| 6,131,584 | A | 10/2000 | Lauterbach |
| 6,162,516 | A | 12/2000 | Derr |
| 6,216,706 | B1 | 4/2001 | Kumar et al. |
| 6,225,483 | B1 | 5/2001 | Franke |
| 6,248,760 | B1 | 6/2001 | Wilhelmsen |
| 6,262,284 | B1 | 7/2001 | Khachik |
| 6,280,761 | B1 | 8/2001 | Santus |
| 6,298,858 | B1 | 10/2001 | Coleman, III et al. |
| 6,298,859 | B1 | 10/2001 | Kierulff et al. |
| 6,325,860 | B1 | 12/2001 | Coleman, III |
| 6,403,126 | B1 | 6/2002 | Webster et al. |
| 6,414,172 | B1 | 7/2002 | Garcés et al. |
| 6,417,157 | B1 | 7/2002 | Wadsworth et al. |
| 6,428,624 | B1 | 8/2002 | Coleman, III et al. |
| 6,440,223 | B1 | 8/2002 | Dube et al. |
| 6,495,175 | B2 | 12/2002 | Rao et al. |
| 6,499,489 | B1 | 12/2002 | Coleman, III |
| 6,504,085 | B1 | 1/2003 | Howard |
| 6,591,841 | B1 | 7/2003 | White et al. |
| 6,668,839 | B2 | 12/2003 | Williams |
| 6,676,959 | B1 | 1/2004 | Andersson et al. |
| 6,695,924 | B1 | 2/2004 | Dube et al. |
| 6,772,767 | B2 | 8/2004 | Mua et al. |
| 6,800,318 | B2 | 10/2004 | Kapila et al. |
| 6,834,654 | B2 | 12/2004 | Williams |
| 6,860,998 | B1 | 3/2005 | Wilde |
| 6,895,974 | B2 | 5/2005 | Peele |
| 6,953,040 | B2 | 10/2005 | Atchley et al. |
| 7,025,066 | B2 | 4/2006 | Lawson et al. |
| 7,032,601 | B2 | 4/2006 | Atchley et al. |
| 7,067,718 | B2 | 6/2006 | Anai et al. |
| 7,074,449 | B1 | 7/2006 | Holley et al. |
| 7,156,981 | B2 | 1/2007 | Wilde et al. |
| 7,179,930 | B2 | 2/2007 | Bhaskaran et al. |
| 7,198,808 | B2 | 4/2007 | Krasutsky et al. |
| 7,271,298 | B2 | 9/2007 | Xu et al. |
| 7,337,782 | B2 | 3/2008 | Thompson |

(56) References Cited

U.S. PATENT DOCUMENTS

| | | | |
|---|---|---|---|
| 7,351,424 B2 | 4/2008 | Ornelas-Cravioto et al. |
| 7,374,779 B2 | 5/2008 | Chen et al. |
| 7,615,657 B2 | 11/2009 | Bathurst et al. |
| 7,622,599 B2 | 11/2009 | Swaminathan et al. |
| 7,629,007 B2 | 12/2009 | Peña |
| 7,638,314 B2 | 12/2009 | Zappi et al. |
| 7,652,167 B2 | 1/2010 | Miller et al. |
| 7,667,068 B2 | 2/2010 | Miller et al. |
| 7,671,242 B2 | 3/2010 | Losso et al. |
| 7,694,686 B2 | 4/2010 | Atchley et al. |
| 7,726,320 B2 | 6/2010 | Robinson et al. |
| 7,741,500 B2 | 6/2010 | Arhancet et al. |
| 7,810,507 B2 | 10/2010 | Dube et al. |
| 7,820,419 B2 | 10/2010 | Smith et al. |
| 7,861,728 B2 | 1/2011 | Holton, Jr. et al. |
| 7,901,512 B2 | 3/2011 | Quinter et al. |
| 7,910,209 B2 | 3/2011 | Uchida et al. |
| 7,943,350 B2 | 5/2011 | Vlasenko et al. |
| 8,061,362 B2 | 11/2011 | Mua et al. |
| 8,236,929 B2 | 8/2012 | Cheryan et al. |
| 8,247,423 B2 | 8/2012 | Estok et al. |
| 8,360,072 B2 | 1/2013 | Krauss |
| 8,389,749 B2 | 3/2013 | Dumesic et al. |
| 8,695,609 B2 | 4/2014 | Dube et al. |
| 8,758,561 B2 | 6/2014 | Dittrich et al. |
| 8,807,141 B2 | 8/2014 | Breslin et al. |
| 8,893,725 B2 | 11/2014 | Dube et al. |
| 2001/0016593 A1 | 8/2001 | Wilhelmsen |
| 2002/0197688 A1 | 12/2002 | Pandolfino |
| 2004/0020503 A1 | 2/2004 | Williams |
| 2004/0101543 A1 | 5/2004 | Liu et al. |
| 2004/0118422 A1 | 6/2004 | Lundin et al. |
| 2004/0173228 A1 | 9/2004 | Coleman, III |
| 2005/0061339 A1 | 3/2005 | Hansson et al. |
| 2005/0066986 A1 | 3/2005 | Nestor et al. |
| 2005/0115580 A1 | 6/2005 | Quinter et al. |
| 2005/0143464 A1 | 6/2005 | Matsuyama et al. |
| 2005/0147722 A1 | 7/2005 | Fan et al. |
| 2005/0244521 A1 | 11/2005 | Strickland et al. |
| 2006/0003036 A1 | 1/2006 | Shaath et al. |
| 2006/0120974 A1 | 6/2006 | Mcneight |
| 2006/0191548 A1 | 8/2006 | Strickland et al. |
| 2006/0198873 A1 | 9/2006 | Chan et al. |
| 2007/0007069 A1 | 1/2007 | Hamasaki et al. |
| 2007/0062549 A1 | 3/2007 | Holton, Jr. et al. |
| 2007/0105112 A1* | 5/2007 | Hitchman ............ A21D 8/042 |
| | | 435/6.13 |
| 2007/0137663 A1 | 6/2007 | Taylor et al. |
| 2007/0186942 A1 | 8/2007 | Strickland et al. |
| 2007/0193596 A1 | 8/2007 | Mori et al. |
| 2007/0277432 A1 | 12/2007 | Jackam et al. |
| 2008/0020050 A1 | 1/2008 | Chau et al. |
| 2008/0029110 A1 | 2/2008 | Dube et al. |
| 2008/0029116 A1 | 2/2008 | Robinson et al. |
| 2008/0029117 A1 | 2/2008 | Mua et al. |
| 2008/0173317 A1 | 7/2008 | Robinson et al. |
| 2008/0196730 A1 | 8/2008 | Engstrom et al. |
| 2008/0209586 A1 | 8/2008 | Nielsen et al. |
| 2008/0305216 A1 | 12/2008 | Crawford et al. |
| 2009/0025738 A1 | 1/2009 | Mua et al. |
| 2009/0025739 A1 | 1/2009 | Brinkley et al. |
| 2009/0028803 A1 | 1/2009 | Mishra et al. |
| 2009/0065013 A1 | 3/2009 | Essen et al. |
| 2009/0081291 A1 | 3/2009 | Gin et al. |
| 2009/0234146 A1 | 9/2009 | Cooney et al. |
| 2009/0293889 A1 | 12/2009 | Kumar et al. |
| 2009/0293895 A1 | 12/2009 | Axelsson et al. |
| 2010/0004294 A1 | 1/2010 | Axelsson et al. |
| 2010/0017916 A1 | 1/2010 | Pappan et al. |
| 2010/0018540 A1 | 1/2010 | Doolittle et al. |
| 2010/0018541 A1 | 1/2010 | Gerardi et al. |
| 2010/0037903 A1* | 2/2010 | Coleman, III ........ A24B 15/306 |
| | | 131/278 |
| 2010/0196980 A1 | 8/2010 | Smith et al. |
| 2010/0197029 A1 | 8/2010 | O'Fallon et al. |
| 2010/0239726 A1 | 9/2010 | Pertsovich |
| 2010/0282267 A1 | 11/2010 | Atchley |
| 2010/0286420 A1 | 11/2010 | Akatsuka et al. |
| 2010/0291245 A1 | 11/2010 | Gao et al. |
| 2011/0083683 A1 | 4/2011 | Krauss |
| 2011/0139164 A1 | 6/2011 | Mua et al. |
| 2011/0174323 A1 | 7/2011 | Coleman, III et al. |
| 2011/0247640 A1 | 10/2011 | Beeson et al. |
| 2011/0259353 A1 | 10/2011 | Coleman, III et al. |
| 2011/0315154 A1 | 12/2011 | Mua et al. |
| 2012/0037175 A1 | 2/2012 | Cantrell et al. |
| 2012/0040408 A1 | 2/2012 | Decker et al. |
| 2012/0055494 A1 | 3/2012 | Hunt et al. |
| 2012/0103353 A1 | 5/2012 | Sebastian et al. |
| 2012/0125354 A1 | 5/2012 | Byrd et al. |
| 2012/0138073 A1 | 6/2012 | Cantrell et al. |
| 2012/0138074 A1 | 6/2012 | Cantrell et al. |
| 2012/0141648 A1 | 6/2012 | Morton et al. |
| 2012/0152265 A1 | 6/2012 | Dube et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. et al. |
| 2012/0260929 A1 | 10/2012 | Coleman et al. |
| 2012/0272976 A1 | 11/2012 | Byrd et al. |
| 2012/0312314 A1 | 12/2012 | Plakidis et al. |
| 2013/0008457 A1 | 1/2013 | Zheng et al. |
| 2013/0014771 A1 | 1/2013 | Coleman, III et al. |
| 2013/0125907 A1 | 5/2013 | Dube et al. |
| 2013/0213417 A1 | 8/2013 | Chong et al. |
| 2013/0255702 A1 | 10/2013 | Griffith, Jr. et al. |
| 2013/0276801 A1* | 10/2013 | Byrd, Jr. .................. C08H 8/00 |
| | | 131/297 |
| 2014/0000638 A1 | 1/2014 | Sebastian et al. |
| 2014/0020694 A1* | 1/2014 | Moldoveanu ............ A01H 5/12 |
| | | 131/280 |
| 2014/0060554 A1 | 3/2014 | Collett et al. |
| 2014/0096780 A1 | 4/2014 | Gerardi |
| 2014/0096781 A1 | 4/2014 | Sears et al. |
| 2014/0096782 A1 | 4/2014 | Ampolini et al. |
| 2014/0190497 A1 | 7/2014 | Dube et al. |
| 2014/0256829 A1 | 9/2014 | Junker |
| 2014/0271951 A1* | 9/2014 | Mua .................... A24B 15/241 |
| | | 424/751 |
| 2014/0271952 A1* | 9/2014 | Mua .................... A24B 15/241 |
| | | 424/751 |
| 2015/0040922 A1 | 2/2015 | Dube et al. |
| 2015/0059780 A1 | 3/2015 | Davis et al. |
| 2015/0201669 A1 | 7/2015 | Junker et al. |

FOREIGN PATENT DOCUMENTS

| | | |
|---|---|---|
| CN | 101262786 | 9/2008 |
| CN | 101450897 | 6/2009 |
| CN | 101801188 | 8/2010 |
| CN | 102079704 | 6/2011 |
| CN | 10218366 | 9/2011 |
| CN | 104 138 029 | 11/2014 |
| EP | 0 244 208 | 11/1987 |
| GB | 996141 | 6/1965 |
| GB | 1 202 821 | 8/1970 |
| GB | 2 020 538 A | 11/1979 |
| JP | 59-28465 A | 2/1984 |
| JP | H08-266260 | 10/1996 |
| JP | 1162008 | 10/1997 |
| JP | H11-308987 | 11/1999 |
| JP | H11-332408 | 12/1999 |
| JP | 2003024096 | 1/2003 |
| JP | 2009527488 | 7/2009 |
| KR | 930003904 | 5/1993 |
| KR | 10-2006-0054728 | 5/2006 |
| KR | 1020120022238 | 3/2012 |
| KR | 101233116 | 2/2013 |
| WO | WO 02/083191 | 10/2002 |
| WO | WO 2004/095959 | 11/2004 |
| WO | WO 2005/004480 | 1/2005 |
| WO | WO 2005/016036 | 2/2005 |
| WO | WO 2005/027892 | 3/2005 |
| WO | WO 2005/041699 | 5/2005 |

(56) References Cited

FOREIGN PATENT DOCUMENTS

| WO | WO 2005/063060 | 7/2005 | |
|---|---|---|---|
| WO | WO 2007/104573 | 9/2007 | |
| WO | WO 2008/092207 | 8/2008 | |
| WO | WO 2009/015142 | 1/2009 | |
| WO | WO 2009/075762 | 6/2009 | |
| WO | WO 2009/110775 A1 | 9/2009 | |
| WO | WO 2010/054198 A2 | 5/2010 | |
| WO | WO 2010/132444 | 11/2010 | |
| WO | WO 2013/158957 | 10/2013 | |
| WO | WO-2015052282 A1 * | 4/2015 | ............. A24B 13/00 |

OTHER PUBLICATIONS

Effect of Treatment of Tobacco with Ammonia or Various Ammonium Salts on the Levels of Pyridines and Pyrazines in Smoke, Truth Tobacco Industry Documents, University of California San Francisco, www.industrydocumentslibrary.ucsf.edu/tobacco/docs/lhvd0152, Published Dec. 10, 2010.*

Recrystallization, University of Toronto, https://web.archive.org/web/20141029140730/http://www.chem.utoronto.ca/coursenotes/CHM249/Recrystallization.pdf, Published Oct. 29, 2014.*

Richard Nakka, "Purification of Low-grade Potassium Nitrate". Richard Nakka's Experimental Rocketry Website, Apr. 3, 2008.*

Paper from tobacco stalks, Epino, M.A., Philippine STAR, https://www.philstar.com/business/agriculture/2004/02/29/240762/paper-tobacco-stalks. (Year: 2004).*

"Enzyme Class Index: Hydrolases on esters", *Sigma-Aldrich*, 2014, [online], Retrieved from the Internet, [retrieved Oct. 21, 2014], URL:http://www.sigmaaldrich.com/life-science/metabolomics/enzyme-explorer/class-index/hydrolases-on-esters.html.

Anonymous, "Cellulosic Sugars—Wikipedia", Nov. 29, 2016, XP055363042, Retrieved from the internet: URL: https://enwikipedia.org/wiki/Cellulosic_sugars [retrieved on Apr. 7, 2017].

Akpinar et al., "Enzymatic Production of Xylooligosaccharide from Selected Agricultural Wastes," *Food and Bioproducts Processing*, 2009, pp. 145-151, vol. 87.

Alonso et al., "Integrated Conversion of Hemicellulose and Cellulose from Lignocellulosic Biomass," *Energy & Environmental Science*, 2013, vol. 6, pp. 76-80.

Brandt et al., "Practical Aspects of Preparative HPLC in Pharmaceutical and Development Production", *LC GC Europe*, Mar. 2002, pp. 2-5.

Bryzgalov et al., "Comparative Life Cycle Assessment of General Loose and Portion Snus", *1N1800 Life Cycle Assessment*, May 26, 2005, pp. 3-23.

Chu et al., "Fatty Acid Composition in Tobacco, I. Green Tobacco Plants", *Plant Physiology*, American Society of Plant Biologists, Mar. 1968, pp. 428-433, vol. 43(3), [online], retrieved from the internet, [retrieved Jun. 24, 2015], URL:http://www.ncbi.nlm.nih.gov/pmc/articles/PMC1086856/.

Clark et al., "Derivatization Solid-Phase Microextraction Gas Chromatographic-Mass Spectrometric Determination of Organic Acids in Tobacco"; 1997; Journal of Chromatographic Science; vol. 35; pp. 209-212.

Coleman, III et al., "Headspace Solid-Phase Microextraction Analysis of Artificial Flavors", *J. Sci. Food Agric.*, 2005, pp. 2645-2654, vol. 85.

Coleman, III et al., "The Use of a Non-Equilibrated Solid Phase Microextraction Method to Quantitatively Determine the Off-Notes in Mint and Other Essential Oils", *J. Sci. Food Agric.*, 2004, pp. 1223-1228, vol. 84.

Crabbe et al., "Biodiesel Production of Crude Palm Oil and Evaluation of Butanol Extraction and Fuel Properties," *Process Biochemistry*, 37, 65-71, (2001).

Ejikeme et al., "Catalysis in Biodiesel Production by Trans-Esterification Processes: An Insight," *Journal Chemistry*, 7, 1120-1132 (2010).

Freedman et al., "Trans-Esterification Kinetics of Soybean Oil," *JAOCS*, 63, 1375-1380 (1986).

Frega et al., "Chemical composition of Tobacco Seeds (*Nicotiana tabacum* L.)," *JAOCS*, 1991, pp. 20-33, vol. 68(1).

Giannelos et al., "Tobacco Seed Oil as an Alternative Diesel Fuel: Physical and Chemical Properties", *Industrial Crops and Products*, 2002, vol. 16, pp. 1-9.

Ishikawa et al., "Water-Soluble Constituents of Dill", *Chem. Pharm. Bull.*, 2002, pp. 501-507, vol. 50, No. 4.

Kodama et al., "Isolation of a New Terpene Glucoside, 3-Hydroxy-5, 6-epoxy-β-ionyl-β-D-glucopyranoside from Flue-cured Tobacco", *Agric. Biol. Chem.*, 1981, pp. 941-944, vol. 45, No. 4.

Kolah et al. (2008), "Triethyl Citrate Synthesis by Reactive Distillation," *Industrial and Engineering Chemistry Research*, vol. 47, No. 4, pp. 1017-1024.

Kolah et al. "Reaction Kinetics of the Catalytic Esterification of Citric Acid with Ethanol", 2007; Industrial Engineering and Chemistry Research; vol. 46; pp. 3180-3187; American Chemical Society.

Leffingwell & Associates, Ester Detection Thresholds and Molecular Structures, www.leffingwell.com/esters, downloaded Sep. 23, 2015.

Leffingwell et al., "Tobacco Flavoring for Smoking Products", *R. J. Reynolds Tobacco Company*, 1972, pp. 1-72.

Li et al. Nanfang Nongye Xuebao. 2012. vol. 43, No. 8, pp. 1158-1163. CAPLUS Abstract enclosed.

Liu et al. J. Henan Agricult. Sci. 2012. vol. 41, No. 9, pp. 50-52. CAPLUS Abstract enclosed.

Loughrin et al., "Glycosidically Bound Volatile Components of *Nicotiana sylvestris* and *N. suaveolens* Flowers", *Phytochemistry*, 1992, pp. 1537-1540, vol. 31, No. 5.

Loughrin et al., "Headspace Compounds from Flowers of *Nicotiana tabacum* and Related Species", *J. Agric. Food Chem.*, 1990, vol. 38, No. 2, pp. 455-460.

Marchetti, J.M., et al., "Possible Methods for Biodiesel Production," Renewable and Sustainable Energy Review, 2007, pp. 1300-1311, vol. 11(6).

Matsumura et al., "Water-Soluble Constituents of Caraway: Carvone Derivatives and their Glucosides", *Chem. Pharm. Bull.*, 2002, pp. 66-72, vol. 50, No. 1.

Matsuzaki et al., "Novel Glycerolipids and Glycolipids from the Surface Lipids of Nicotiana Benthamiana," *Biosci. Biotech. Biochem.*, Mar. 1992, pp. 1565-1569, vol. 56(10).

Moldoveanu et al., "Dual Analysis of Triglycerides from Certain Common Lipids and Seed Extracts," *J. Agric.Food Chem.*, 59, 2137-2147 (2011).

Moldoveanu, "5. Profiling of lipids from fruit and seed extracts", Lipidomics: Sea Food, Marine Based Dietary Supplement, *Fruit and Seed*, 2012: pp. 73-123, Ed. Su Chen [online], Retrieved from the Internet, [retrievedOct. 21, 2014], URL:http://www.tmres.com/ebook/uploads/snchencontent/T_13743193085%20Su%20Chen.pdf.

Mukhtar et al., "Fatty Acid Composition of Tobacco Seed Oil and Synthesis of Alkyd Resin", *Chin. J. of Chem.*, 2007, vol. 25, No. 5, pp. 705-708.

Ochiai, N., "6 Times Faster Screening of Pesticide Multi-Residues in Aqueous Samples Take Two!" *Gerstel Solutions Worldwide*, 2006, pp. 17-19, No. 6.

Patel et al., "Production Potential and Quality Aspects of Tobacco Seed Oil", *Tob. Res.*, 1998, vol. 24, No. 1, pp. 44-49.

Perflavory Information System, www.perflavory.com, downloaded Sep. 23, 2015.

Raguso et al., "Fragrance Chemistry, Nocturnal Rhythms and Pollination "Syndromes" in *Nicotiana*", *Phytochemistry*, 2003, pp. 265-284, vol. 63.

Ralph et al., "NMR Characterization of Altered Lignins Extracted from Tobacco Plants Down-Regulated for Lignification Enzymes Cinnamyl-Alcohol Dehydrogenase and Cinnamoyl-CoA Reductase," *Proceedings of the National Academy of Sciences*, 1998, vol. 95, pp. 12803-12808. http://www.ncbi.nlm.nih.gov/pmc/articles/PMC23601/.

Sadecka, et al.; Determination of organic acids in tobacco by capillary isotachophoresis; 2003; Journal of Chromatography A; vol. 988; pp. 161-165; Elsevier Science B.V.

(56) References Cited

OTHER PUBLICATIONS

Sahraoui et al., "Improved Microwave Steam Distillation Apparatus for Isolation of Essential Oils Comparison with Conventional Steam Distillation", *J. Chromatogr. A.*, 2008, pp. 229-233.
Satynaryana Murthy, "Performance of Tobacco Oil Based Bio-Diesel Fuel in a Single cylinder Direct Injection Engine," *International J. Physical Sci.*, 5, 2066-2074 (2010).
Schuchardt et al., "Trans-Esterification of Vegetable Oils: A Review," Chem. Soc., 9, 199-210 (1998).
Shmuk (1934), "The Method of Determination of Citric and Malic Acids in Tobacco and Makhorka" Ibid., pp. 247-251.
Shmuk et al. (1930), "Investigation of the Tobacco Acids," in Works of Academician A.A. Shmuk, vol. III, The Chemistry and Technology of Tobacco (Moscow: Pishchepromidzat, 1953; Jerusalem: trans. Lengy et al., Israel Program for Scientific Translations, 1961), pp. 136-144.
Shmuk et al. (1933), "Tobacco and Makhorka As Raw Materials for the Production of Citric Acid," in Works, op. cit., pp. 688-707.
Siti Solehah et al. "Effect of Temperature and pH on Glucose Production Using Enzymatic Hydrolysis," Apr. 1, 2010, XP055363092, Retrieved from the Internet: URL: http://umpir.ump.edu.my/3287/1/CD5873_SITI-SOLEHAH_AHMAD.pdf [Retrieved on Apr. 7, 2017].
Snook et al., "The Flower Flavonols of *Nicotiana* Species", *Phytochemistry*, 1992, pp. 1639-1647, vol. 31, No. 5.
Stanesh, *Biochemistry*, Chapter 6. Lipids and Membranes, Springer Science+Business Media, 1998, pp. 141-144.
Stanisavljevic et al., "Comparison of techniques for the Extraction of Tobacco Seed Oil", *Eur. J. Lipid Sci. Technol.*, 2009, vol. 111, pp. 513-518.
Stanisavljević et al., "Ultrasonic extraction of oil from tobacco (*Nicotiana tabacum* L.) seeds", *Ultrasonics Sonochemistry*, 2007, pp. 646-652, vol. 14, No. 5.
Tashpulatov, et al., "Enzymatic Production of Glucose Syrups from Cellulose-Containing Plant Wastes," *Chemistry of Natural Compounds*, vol. 33, No. 3, 1997.
Tienpont et al., "Stir Bar Sorptive Extraction-Thermal Desorption-Capillary GC-MS Applied to Biological Fluids", *Anal. Bioanal. Chem..*, 2002, pp. 46-55, vol. 373.
Tso (1972), Physiology and Biochemistry of Tobacco Plants (Stroudsburg: Dowden, Hutchinson and Ross), p. 205.
TurboVap® II brochure, Biotage, 2010, [online], retrieved from the Internet, [retrieved Dec. 1, 2015], URL:http://www.google.com/url?sa=t&rct=j&q=&esrc=s&source=web&ed=11&ved=oahUKEwiKyOzrh7vJAhULx2MKHOYRA11OFghKMAo&url=http%3A%2F%2Fwww.uniscience.com.br%2Fcorantes-fluorescentes-de-membrana-biotium%2Fdioc5-3-3-3-dipentyloxacarbocyanine-iodide-bio . . . .
Veljkovic, V. B., et al., "Biodiesel Production from Tobacco Seed Oil with a High Content of Free Fatty Acids," *Fuel*, 2006, pp. 2671-2675, vol. 85(17).
Vickery et al. The Non-Volatile Organic Acids of Green Tobacco Leaves; 1931; Journal of Biological Chemistry; vol. 90; pp. 637-653.
Winayanuwattikun, P., et al., "Potential Plant Oil Feedstock for Lipase-Catalyzed Biodiesel Production in Thailand," Biomass and Bioenergy, 2008, pp. 1279-1286, vol. 32(12).
Wu et al. Yunnan Nongye Daxue Xuebao. 2013. vol. 28, No. 3, pp. 353-359. CAPLUS Abstract enclosed.
Xi et al. Yancao Keji. 2011. vol. 5, pp. 29-33. CAPLUS Abstract enclosed.
Zhang et al., "Advances in the Catalytic Production and Utilization of Sorbitol," *Industrial & Engineering Chemistry Research*, 2013, vol. 52, p. 11799-11815.
Zhang, Yi-Heng Percival et al., "Toward an Aggregated Understanding of Enzymatic Hydrolysis of Cellulose: Noncomplexed Cellulase Systems," Wiley InterScience. Biotechnology and Bioengineering, vol. 88, No. 7, Dec. 30, 2004, p. 797-824.
Ziaie-Shirkolaee et al. "Study on Cellulose Degradation During Organosolv Delignification of Wheat Straw and Evaluation of Pulp Properties," *Iranian Polymer Journal*, 2007, pp. 83-96, vol. 16(2).

\* cited by examiner

TOBACCO-DERIVED FLAVORANTS

FIELD OF THE INVENTION

The present invention relates to products made or derived from tobacco, or that otherwise incorporate tobacco or components of tobacco. Of particular interest are ingredients or components obtained or derived from a plant of the *Nicotiana* species.

BACKGROUND OF THE INVENTION

Cigarettes, cigars, and pipes are popular smoking articles that employ tobacco in various forms. Such smoking articles are employed by heating or burning tobacco to generate aerosol (e.g., smoke) that may be inhaled by the smoker. Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3$^{rd}$ Ed., p. 43 (1990) and *Tobacco Production, Chemistry and Technology*, Davis et al. (Eds.) p. 346 (1999).

Tobacco also may be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2005/0244521 to Strickland et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; 2008/0196730 to Engstrom et al.; 2008/0209586 to Neilsen et al.; 2008/0305216 to Crawford et al.; 2009/0025738 to Mua et al.; 2009/0025739 to Brinkley et al.; 2009/0065013 to Essen et al.; 2009/0293889 to Kumar et al.; 2010/0018540 to Doolittle et al; 2010/0018541 to Gerardi et al.; 2010/0291245 to Gao et al; 2011/0139164 to Mua et al.; 2011/0174323 to Coleman, III et al.; 2011/0247640 to Beeson et al.; 2011/0259353 to Coleman, III et al.; 2012/0037175 to Cantrell et al.; 2012/0055494 to Hunt et al.; 2012/0103353 to Sebastian et al.; 2012/0125354 to Byrd et al.; 2012/0138073 to Cantrell et al.; and 2012/0138074 to Cantrell et al; PCT WO 04/095959 to Arnarp et al.; PCT WO 05/063060 to Atchley et al.; PCT WO 05/004480 to Engstrom; PCT WO 05/016036 to Bjorkholm; PCT WO 05/041699 to Quinter et al., and PCT WO 10/132444 to Atchley; each of which is incorporated herein by reference.

One type of smokeless tobacco product is referred to as "snuff." Representative types of moist snuff products, commonly referred to as "snus," have been manufactured in Europe, particularly in Sweden, by or through companies such as SWEDISH MATCH® AB, FIEDLER & LUNDGREN® AB, GUSTAVUS® AB, SKANDINAVISK TOBAKSKOMPAGNI® A/S, and ROCKER PRODUCTION® AB. Snus products available in the U.S.A. have been marketed under the tradenames CAMEL® Snus Frost, CAMEL® Snus Original and CAMEL® Snus Spice by R.J. REYNOLDS TOBACCO COMPANY®. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames OLIVER TWIST® by HOUSE OF OLIVER TWIST® A/S; COPENHAGEN® moist tobacco, COPENHAGEN ® pouches, SKOAL® Bandits, SKOAL® Pouches, SKOALDRY®, ROOSTER®, RED SEAL® long cut, HUSKY®, and REVEL® Mint Tobacco Packs by U.S. SMOKELESS TOBACCO COMPANY ®; MARLBORO® Snus and "taboka" by PHILLIP MORRIS® USA; LEVI GARRETT®, PEACHY®, TAYLOR'S PRIDE®, KODIAK®, HAWKEN WINTERGREEN®, GRIZZLY®, DENTAL®, KENTUCKY KING®, and MAMMOTH CAVE® by AMERICAN SNUFF COMPANY®, LLC; CAMEL® Snus, CAMEL® Orbs, CAMEL® Sticks, and CAMEL® Strips by R.J. REYNOLDS TOBACCO COMPANY®. Other exemplary smokeless tobacco products that have been marketed include those referred to as KAYAK® moist snuff and CHATANOOGA CHEW® chewing tobacco by SWISHER INTERNATIONAL®, Inc; and REDMAN® chewing tobacco by PINKERTON TOBACCO COMPANY® LP.

It would be desirable to provide additional uses for the portions of the tobacco plant commonly viewed as waste. In particular, it would be advantageous to develop products derived entirely from a plant of the *Nicotiana* species.

SUMMARY OF THE INVENTION

The present invention provides methods of forming pyrazines from reactants derived from a harvested plant of the

*Nicotiana* species. A method of forming pyrazines from reactants derived from a plant of the *Nicotiana* species can comprise receiving a reactant solution comprising at least one tobacco-derived carbon source (e.g., tobacco-derived cellulosic sugar) and at least one tobacco-derived nitrogen source (e.g, tobacco-derived protein and/or a tobacco-derived amino acid), heating the reactant solution to a reactant temperature and holding the reactant solution at the reactant temperature for a time sufficient to produce a reactant product comprising at least one tobacco-derived pyrazine, and isolating the at least one tobacco-derived pyrazine from the reactant product. The step of isolating the at least one tobacco-derived pyrazine from the reactant product can comprise at least one of liquid-liquid extraction of the reactant product, liquid-solid extraction of the reactant product, and simple distillation of the reactant product, for example. The at least one tobacco-derived pyrazine can be selected from the group consisting of pyrazine, 2-methylpyrazine, 2,5-dimethylpyrazine, 2,6-dimethylpyrazine, 2-ethylpyrazine, 2,3-dimethylpyrazine, 2,3,5-trimethylpyrazine, 2-ethyl-6-methylpyrazine, 2-ethyl-5-methylpyrazine, 2-ethyl-3-methylpyrazine, vinylpyrazine, 2-ethyl-3,6-dimethylpyrazine, 2-ethyl-3,5-dimethylpyrazine, 2-methyl-6-vinylpyrazine, 2,6-diethyl-3-methylpyrazine, 2-isoamylpyrazine, 2-isoamyl-6-methylpyrazine, 2-phenylethylpyrazine, and combinations thereof.

In various embodiments, the method of forming tobacco-derived pyrazines can further include receiving a cellulosic biomass derived from a plant of the *Nicotiana* species (e.g., tobacco material comprising at least one of a stalk material and a root material, flowers, stems, leaves, etc. of a harvested plant of the *Nicotiana* species), delignifying the tobacco material to form a tobacco-derived pulp, hydrolyzing the tobacco-derived pulp to form a hydrolyzed tobacco product comprising residual solids and a liquid comprising the least one tobacco-derived cellulosic sugar, and separating the liquid comprising the least one tobacco-derived cellulosic sugar from the residual solids. In various embodiments, the cellulosic biomass can comprise residual biomass left behind from other processes that utilize tobacco material (e.g., extraction processes, cutting parts of the plant for use in tobacco products, etc.). In certain embodiments, the tobacco material can comprise at least about 90 percent by dry weight of at least one of the stalk material and the root material of the harvested plant of the *Nicotiana* species, for example. In various embodiments, the step of hydrolyzing the tobacco-derived pulp can comprise enzymatic saccharification of the tobacco-derived pulp in the presence of at least one enzyme.

In various embodiments, an Organosolv process can be used to isolate cellulose materials from tobacco materials. Cellulosic sugars can then be derived from the cellulose materials via enzymatic hydrolysis, for example. As such, methods of the present invention can further comprise receiving a tobacco material comprising a harvested plant of the *Nicotiana* species, treating the tobacco material in aqueous butanol with a solid to solvent weight ratio of about 1:5 to about 1:10 to form a tobacco-derived pulp, hydrolyzing the tobacco-derived pulp to form a hydrolyzed tobacco product comprising residual solids and a liquid comprising the least one tobacco-derived cellulosic sugar, and separating the liquid comprising the least one tobacco-derived cellulosic sugar from the residual solids. The step of treating the tobacco material in aqueous butanol can comprise adding an amount of sulfuric acid sufficient to drop the pH of the tobacco material and aqueous butanol to about 2 or lower. In some embodiments, the step of treating the tobacco material in aqueous butanol can comprise heating the tobacco material and aqueous butanol to about 175° C. or greater, and stirring the tobacco material and aqueous butanol for about 30 min or longer (e.g., about 30 mins to about 60 min).

In some embodiments, the method of forming tobacco-derived pyrazines can further comprise evaporating at least a portion of the liquid comprising the at least one tobacco-derived cellulosic sugar to form a condensed syrup. The condensed syrup can comprise at least about 80% by weight glucose, for example. In various embodiments, the method can further include isomerizing the glucose to produce high fructose tobacco syrup using glucose isomerase.

In various embodiments, the method of forming tobacco-derived pyrazines can further comprise providing at least one tobacco-derived nitrogen source by receiving a protein-enriched material from a plant of the *Nicotiana* species or portion thereof, and hydrolyzing the protein-enriched material to produce a hydrolyzed product which may comprise at least one tobacco-derived amino acid. In certain embodiments, the step of hydrolyzing the protein-enriched material can comprise enzymatic hydrolysis of the protein-enriched material in the presence of at least one enzyme. In some embodiments, the method can further include receiving a plant material of the *Nicotiana* species, contacting the plant material with a solvent for a time and under conditions sufficient to extract one or more proteins from the plant material into the solvent and form a liquid protein-containing extract, separating a solid extracted plant material from the liquid protein-containing extract, clarifying the liquid protein-containing extract to form a clarified protein-containing extract and a solids fraction, and treating the clarified protein-containing extract so as to provide the protein-enriched material comprising at least about 60% protein by dry weight. The treating step can comprise, for example, adjusting the pH of the clarified protein-containing extract to a pH of less than about 6 to form an acidic extract, isolating a precipitate from the acidic extract, and washing the precipitate to provide the protein-enriched material. In certain embodiments, the pH of the clarified protein-containing extract can be adjusted to a pH of between about 4.5 to about 6 to provide a RuBisCO-containing protein-enriched material.

Various embodiments of methods described herein can further include adding tobacco-derived ammonium ions to the reactant solution. In some embodiments, the methods can further comprise electrochemically reducing tobacco-derived potassium nitrate crystals to form the tobacco-derived ammonium hydroxide. Furthermore, the methods can also include receiving a tobacco biomass comprising a harvested plant of the *Nicotiana* species, extracting the tobacco biomass in about a 10:1 to about a 1:10 ratio of water to tobacco biomass at an elevated temperature to form a tobacco extract and fibrous tobacco solids, separating the tobacco extract from the fibrous tobacco solids, filtering the separated tobacco extract to form a filtered extract, concentrating the filtered extract to form a concentrated extract, cooling the concentrated extract to a temperature of about −5° C. to about 5° C. for about 12 hours or longer to generate the tobacco-derived potassium nitrate crystals and a residual mother liquid. In some embodiments, the methods can further comprise separating the tobacco-derived potassium nitrate crystals and the residual mother liquid, and re-cooling the residual mother liquid to a temperature of about −5° C. to about 5° C. for about 12 hours or longer to generate a second batch of the tobacco-derived potassium nitrate crystals and residual mother liquid. In certain embodiments, the methods can further comprise separating the tobacco-derived potassium nitrate crystals and the residual mother liquid, dissolving the tobacco-derived potassium nitrate crystals in water, filtering the dissolved tobacco-derived potassium nitrate crystals to remove tobacco solids and form a second filtered tobacco extract, concentrating the second filtered tobacco extract to form a second concentrated extract, cooling the second concentrated extract to a temperature of about −5° C. to about 5° C. for about 12 hours or longer to generate purified tobacco-derived potassium nitrate crystals and a purified residual mother liquid.

The methods of the present invention can further comprise incorporating at least one tobacco-derived pyrazine into a tobacco product. In certain embodiments, the tobacco product can be a smoking article.

The present invention also provides a tobacco-derived pyrazine derived from heating an aqueous solution comprising at least one tobacco-derived cellulosic sugar, at least one tobacco-derived amino acid and tobacco-derived ammonium hydroxide. A tobacco product incorporating the tobacco-derived pyrazine is also provided herein.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION

Figure 1A:
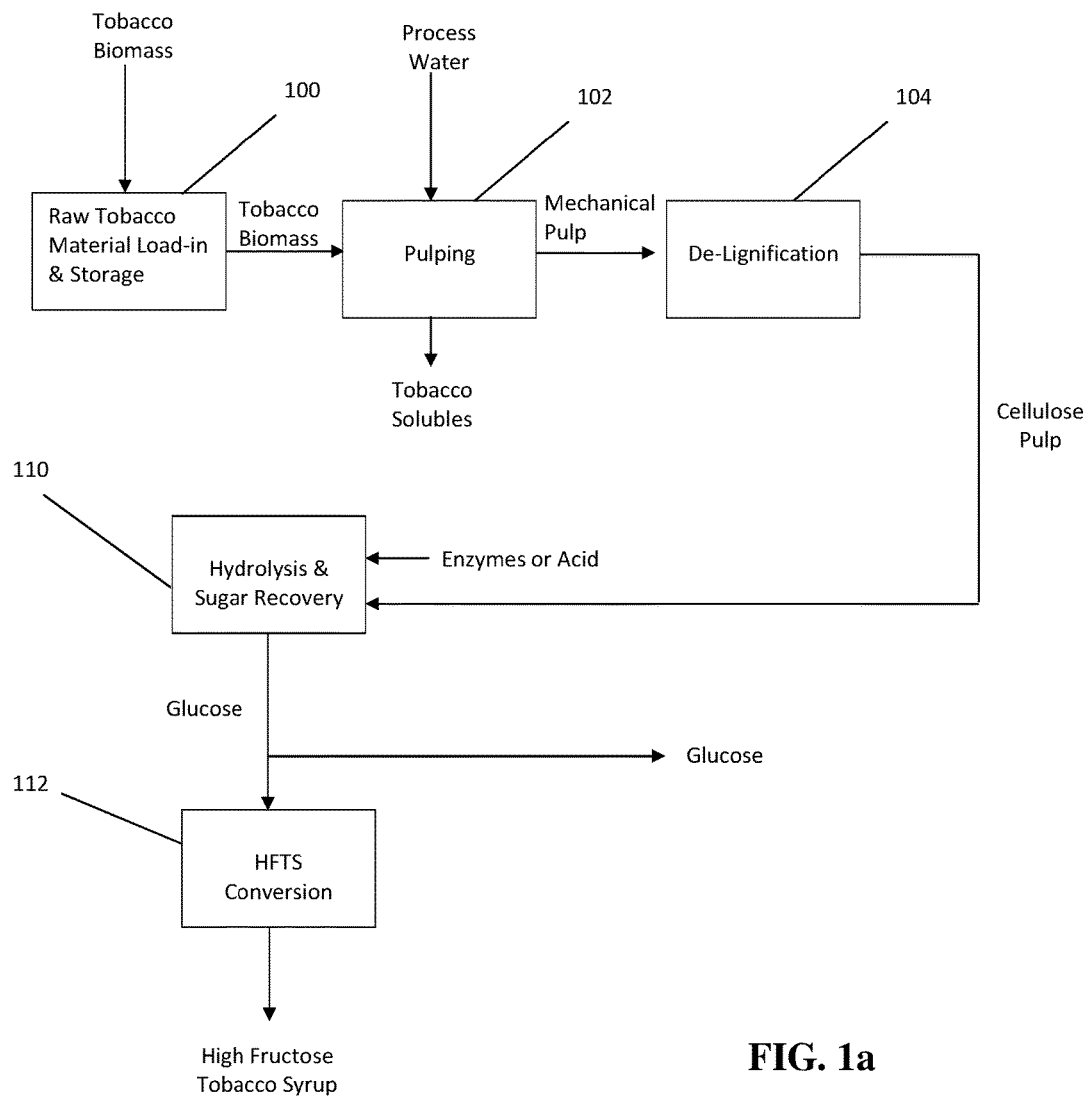
FIG. 1a is a flow chart describing methods of forming cellulosic sugars and optional downstream products from tobacco biomass materials.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention provides methods of forming pyrazines from reactants derived from a harvested plant of the *Nicotiana* species. Pyrazines are formed by heating mixtures of carbon sources and nitrogen sources. In various embodiments of the present invention, the formation of tobacco-derived pyrazines has been optimized using at least one tobacco-derived sugar (e.g., high fructose tobacco syrup (HFTS)) as the carbon source and tobacco-derived protein and/or amino acids derived from the hydrolysis of tobacco-derived protein as the nitrogen source. In various embodiments, the protein can be in the form of ribulose-1,5-bisphosphate carboxylase (Rubisco), which is present in the tobacco plant. Methods of isolating the tobacco-derived reactants and methods of then producing tobacco-derived pyrazines are discussed in more detail below.

Tobacco Materials

The present disclosure is applicable, in some embodiments, for large scale production, where the term large scale production refers to processing large quantities of a biomass (e.g., tobacco) on a mass production level. The term "biomass" and related terms such as "biomatter" and "plant source" are understood to refer to any portion of a harvested plant that may be processed to extract, separate, or isolate components of interest therefrom. The processing may be carried out in relation to various plants or portions thereof, such as seeds, flowers, stalks, stems, roots, tubers, leaves, or any further portions of the plant.

The selection of the plant from the *Nicotiana* species utilized in the methods of the invention can vary; and in particular, the types of tobacco or tobaccos can vary. The type of tobacco used as the source of input material for each component described herein can vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative types of plants from the *Nicotiana* species are set forth in Goodspeed, *The*

*Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference.

The particular *Nicotiana* species of material used in the invention could also vary. Of particular interest are *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata,* and *N. x sanderae*. Also of interest are *N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. rustica, N. simulans, N. stocktonii, N. suaveolens, N. tabacum, N. umbratica, N. velutina,* and *N. wigandioides*. Other plants from the *Nicotiana* species include *N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia* and *N. spegazzinii*. The *Nicotiana* species can be derived using genetic-modification or crossbreeding techniques (e.g., tobacco plants can be genetically engineered or crossbred to increase or decrease production of certain components or to otherwise change certain characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al.; and U.S. Pat. No. 7,230,160 to Benning et al.; US Patent Appl. Pub. No. 2006/0236434 to Conkling et al.; and PCT WO 2008/103935 to Nielsen et al.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *Nicotiana* species. See, for example, the portions of tobacco plants set forth in US Pat. Appl. Pub. Nos. 2011/0174323 to Coleman, III et al. and 2012/0192880 to Dube et al., which are incorporated by reference herein.

The plant component or components from the *Nicotiana* species can be employed in an immature form. That is, the plant can be harvested before the plant reaches a stage normally regarded as ripe or mature. As such, for example, the plant can be harvested when the tobacco plant is at the point of a sprout, is commencing leaf formation, is commencing flowering, or the like.

The plant components from the *Nicotiana* species can be employed in a mature form. That is, the plant can be harvested when that plant reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position.

After harvest, the plant of the *Nicotiana* species, or portion thereof, can be used in a green form (e.g., tobacco can be used without being subjected to any curing process). In various embodiments, the tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. In some embodiments, harvested tobacco can be sprayed with a buffer or antioxidant (e.g., a sodium metabisulfite buffer) to prevent the green plants from browning prior to further treatment as described herein. Other exemplary processing techniques are described, for example, in US Pat. Appl. Pub. Nos. 2009/0025739 to Brinkley et al. and 2011/0174323 to Coleman, III et al., which are incorporated by reference herein. At least a portion of the plant of the *Nicotiana* species can be treated with enzymes and/or probiotics before or after harvest, as discussed in US Pat. Appl. Pub. Nos. 2013/0269719 to Marshall et al., and 2014/0020694 to Moldoveanu, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). Although any single part of the tobacco plant or multiple parts of the tobacco plant can be used according to the present invention, preferably tobacco stalk, tobacco leaves, or both tobacco stalk and leaves are used. The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). For example, in certain embodiments, tobacco stalk, either alone or in combination with other portions of the plant (e.g., stalk and leaf together) can be used and may, in some embodiments, be subjected to the types of treatment described in US Pat. Appl. Publ. No. 2012/0152265 to Dube et al., which is incorporated herein by reference.

In certain embodiments, the tobacco material can be treated with water to extract an aqueous soluble component of the tobacco material therefrom. In some preferred embodiments, the particulate or powder tobacco material can be combined with water to form a moist aqueous material (e.g., in the form of a suspension or slurry) and the resulting material is typically heated to effectuate extraction of various compounds. The water used to form the moist material can be pure water (e.g., tap water or deionized water) or a mixture of water with suitable co-solvents such as certain alcohols. In certain embodiments, the amount of water added to form the moist material can be at least about 50 weight percent, or at least about 60 weight percent, or at least about 70 weight percent, based on the total weight of the moist material. In some cases, the amount of water can be described as at least about 80 weight percent or at least about 90 weight percent.

The extract thus produced may comprise some level of solid (insoluble) material entrained in the liquid. Accordingly, "extract" is intended to mean the material obtained upon contacting the tobacco material with water and may comprise both soluble components dissolved therein and solid dispersed components. Following the extraction process, the extracted liquid component is typically filtered to remove at least some of the solids. In other words, some or all of the portion of the tobacco material insoluble in the aqueous solvent is removed. The process of filtration can comprise passing the liquid through one or more filter screens to remove selected sizes of particulate matter. Screens may be, for example, stationary, vibrating, rotary, or any combination thereof. Filters may be, for example, press filters or pressure filters. In some embodiments, the filtration method used can involve microfiltration, ultrafiltration, and/or nanofiltration. A filter aid can be employed to provide effective filtration and can comprise any material typically used for this purpose. For example, some common filter aids include cellulose fibers, perlite, bentonite, diatomaceous earth, and other silaceous materials. To remove solid components, alternative methods can also be used, for example, centrifugation or settling/sedimentation of the components and siphoning off of the liquid. See, for example, the processes and products described in U.S. Pat. App. Pub. Nos. 2012/0152265 to Dube et al. and 2012/0192880 to Dube et al., herein incorporated by reference in their entireties. The extracted solid components can be used as the starting tobacco material in various embodiments of the invention described herein.

Cellulosic Sugars Derived from Tobacco Materials

According to the present invention, sugars derived from tobacco materials can serve as the tobacco-derived carbon source in a pyrazine reaction. As discussed in U.S. patent application Ser. No. 14/688,522, filed Apr. 16, 2015, and herein incorporated by reference, methods of forming cellulosic sugars from a plant of the *Nicotiana* species can comprise: i) receiving a tobacco material comprising a harvested plant of the *Nicotiana* species; ii) delignifying the tobacco material to form a tobacco-derived pulp; and iii) hydrolyzing the tobacco-derived pulp to form a hydrolyzed tobacco product comprising residual solids and a liquid comprising at least one tobacco-derived cellulosic sugar. As illustrated at operation 100 of FIG. 1a, for example, preparation of a tobacco material according to the present invention can comprise harvesting a plant from the *Nicotiana* species and, in certain embodiments, separating certain components from the plant such as the stalks and/or roots, and physically processing these components. Although whole tobacco plants or any component thereof (e.g., leaves, flowers, stems, roots, stalks, and the like) could be used in the invention, it can be advantageous to use stalks and/or roots of the tobacco plant. For example, in certain embodiments, the tobacco material from which the cellulosic sugar component is derived comprises at least about 90%, at least about 92%, at least about 95%, or at least about 97% by dry weight of at least one of the stalk material and the root material of a harvested plant of the *Nicotiana* species. The remainder of the description related to cellulosic sugars derived from tobacco material focuses on use of stalks and/or roots from the plant, but the invention is not limited to such embodiments.

The tobacco stalks and/or roots can be separated into individual pieces (e.g., roots separated from stalks, and/or root parts separated from each other, such as big root, mid root, and small root parts) or the stalks and roots may be combined. By "stalk" is meant the stalk that is left after the leaf (including stem and lamina) has been removed. "Root" and various specific root parts useful according to the present invention may be defined and classified as described, for example, in Mauseth, Botany: An Introduction to Plant Biology: Fourth Edition, Jones and Bartlett Publishers (2009) and Glimn-Lacy et al., Botany Illustrated, Second Edition, Springer (2006), which are incorporated herein by reference. The harvested stalks and/or roots are typically cleaned, ground, and dried to produce a material that can be described as particulate (i.e., shredded, pulverized, ground, granulated, or powdered). As used herein, stalks and/or roots can also refer to stalks and/or roots that have undergone an extraction process to remove water soluble materials. The cellulosic material (i.e., pulp) remaining after stalks and/or root materials undergo an extraction process can also be useful in the present invention.

The roots and stalks of a tobacco plant have a higher weight percentage of cellulosic content than tobacco stems. As a result, the roots and stalks of a tobacco plant have a higher sugar yield potential than tobacco stems. Additionally, tobacco stems represent a valuable starting material for the preparation of tobacco reconstituted sheet and expanded stem materials used in tobacco products. Use of tobacco stems as a source for cellulosic sugars would decrease the supply of tobacco stems that can be used in other tobacco manufacturing processes. Tobacco stalks and roots represent a tobacco material not otherwise used in tobacco manufacturing and as such, represent an excellent raw material for the preparation of tobacco-derived cellulosic sugar. An additional tobacco raw material that is otherwise not used in tobacco manufacturing is so-called tobacco dust (i.e., a very small particle tobacco material collected during cigarette manufacturing) and so-called stemmery dust (i.e., a tobacco-derived material collected during the stemming of the tobacco leaves). Tobacco dust and stemmery dust can also be used to produce a cellulosic sugar.

Preferably, the physical processing step comprises comminuting, grinding, and/or pulverizing stalks and/or roots from a *Nicotiana* plant into particulate form using equipment and techniques for grinding, milling, or the like. In certain preferred embodiments, the stalks and/or roots are dried prior to the physical processing step, and thus are relatively dry in form during grinding or milling. For example, the stalks and/or roots can be ground or milled when the moisture content thereof is less than about 15 weight percent or less than about 5 weight percent. In such embodiments, equipment such as hammer mills, cutter heads, air control mills, or the like may be used.

The tobacco material provided following the comminuting, grinding, and/or pulverizing of *Nicotiana* stalks and/or roots can have any size. The tobacco material can be such that parts or pieces thereof have an average width and/or length between about 1/16 inch to about 2 inches, about 1/4 inch to about 1 inch, or about 1/4 inch to about 1/2 inch. In some embodiments, the average width and/or length of the tobacco material is greater than or equal to about 1/8 inches, greater than or equal to about 1/4 inch, greater than or equal to about 1/2 inch, greater than or equal to about 1 inch, or greater than or equal to about 2 inches.

The exact composition of the tobacco material used to produce cellulosic sugars can vary. The composition may depend, in part, on whether the tobacco material is prepared from *Nicotiana* stalks, roots, or a combination thereof. Tobacco material prepared solely from material obtained from *Nicotiana* stalks may exhibit different characteristics than tobacco material prepared solely from material obtained from *Nicotiana* roots. Similarly, tobacco material prepared from material obtained from certain parts of one of these components may exhibit different characteristics than material obtained from other parts of this component (e.g., tobacco material prepared from mid-root material may be different from tobacco material prepared from big root material). For example, in certain embodiments, tobacco material derived from *Nicotiana* stalk has a higher content of volatile compounds than tobacco material derived from *Nicotiana* root.

In various embodiments of the present invention, the tobacco material can be converted into a cellulose material through delignification of the tobacco material, for example. Delignification of tobacco materials can involve a number of operations. See, e.g., U.S. patent application Ser. No. 14/688,522, filed Apr. 16, 2015, and herein incorporated by reference in its entirety. As an initial step, tobacco biomass can undergo a pulping process. Pulps can be produced from raw materials either mechanically or chemically, as illustrated at operation 102 in FIG. 1*a*, for example. As illustrated at operation 104 of FIG. 1, for example, the tobacco-derived pulp can undergo a de-lignification process (e.g., an acid or a base can be used to hydrolyze the tobacco-derived pulp and separate the lignin). In addition, the pulp can be rinsed with water and dewatered at least once. The pulp can be dewatered by wet classification, centrifugation, filtration, or similar liquid separation processes. A centrifuge or other similar equipment can help with pulp and syrup (i.e., solids and liquid) separations. See, e.g., the equipment disclosed in U.S. Pat. No. 521,104 to Davis, U.S. Pat. No. 3,168,474 to Stallman et al., U.S. Pat. No. 5,713,826 to West, and U.S. Pat. No. 7,060,017 to Collier, each of which is herein incorporated by reference in its entirety. For example, a basket centrifuge can be useful to help with the pulp dewatering and lignin syrup recovery activities. In addition, the pulp can then be rinsed one or more times and the pH can be adjusted to a range of about 4.5 to about 5.5. In a preferred embodiment, the pH can be adjusted to about 4.8. The pulp can be dewatered after each rinse.

In some embodiments, the method of producing a tobacco-derived cellulose material can include one or more additional operations. See, e.g., U.S. Patent Appl. Pub. No. 2013/0276801 to Byrd Jr. et al., herein incorporated by reference in its entirety. For example, the tobacco input can undergo further processing steps prior to pulping and/or the delignification method can include additional treatment steps (e.g., drying the tobacco input, depithing the tobacco input, milling the tobacco input, etc.). In some embodiments, these additional steps can be conducted to remove pith from the tobacco input and/or tobacco pulp manually, and thus reduce the amount of chemicals necessary to delignify the tobacco input during a chemical pulping process, for example. Mixing water with the tobacco pulp to form a slurry and filtering the slurry can be conducted, for example, to remove some of the non-cellulosic materials, such as pith, parenchyma, and tissue from the tobacco pulp. Additional treatment steps (e.g., milling the tobacco input) can be conducted to increase the surface area of the tobacco input such that the efficacy of a pulping and/or a bleaching operation is increased. Steam- or water-based pre-hydrolysis of the tobacco stalk prior to pulping, for example, can reduce the amount of chemicals necessary in a bleaching operation. Anthraquinone can be employed in a chemical pulping method in an attempt to provide a higher yield by protecting carbohydrates from the strong base during delignification, for example. Other processing steps known in the pulping and delignification field can be employed in forming cellulosic materials from the raw tobacco input.

After delignifying tobacco biomass, the cellulose material can undergo at least one saccharification process, as illustrated at operation 110 of FIG. 1*a*, for example. Any form of hydrolysis known in the art can be used to break carbohydrates in the tobacco-derived cellulose material into component sugar molecules. In certain embodiments, a salt of a weak acid or a weak base (or both) can be dissolved in water in a hydrolysis process. Acid-base-catalyzed hydrolyses can also be used, for example. In various embodiments, cellulosic materials can undergo enzymatic hydrolysis to form glucose. See, for example, the discussion of enzymatic hydrolysis of cellulose presented in Zhang, Yi-Heng Percival et al., Toward an Aggregated Understanding of Enzymatic Hydrolysis of Cellulose: Noncomplexed Cellulase Systems. Wiley InterScience. Biotechnology and Bioengineering, Vol. 88, No. 7, Dec. 30, 2004, p. 797-824. Generally, cellulose enzyme systems can hydrolyze cellulosic materials. The insoluble cellulosic material can undergo three processes simultaneously: (i) chemical and physical changes in the residual solid-phase cellulose; (ii) primary hydrolysis of the solid phase cellulose to form intermediate products comprising cellobiose, soluble cellodextrins and glucose; and (iii) secondary hydrolysis involving the hydrolysis of soluble intermediates to lower molecular weight intermediates, and ultimately to a liquid phase product comprising glucose. Accordingly, hydrolyzing the tobacco-derived cellulose material can result in a hydrolyzed tobacco product (i.e., a liquid mash) comprising residual solids and a liquid comprising at least one tobacco-derived cellulosic sugar. In various embodiments, the at least one tobacco-derived cellulosic sugar can include glucose, xylose, and combinations thereof.

In various embodiments, the enzyme used for saccharification can comprise CELLIC® CTec 2 (produced by NOVOZYMES® A/S).CELLIC® CTec 2 is an effective cellulase/hemicellulose enzyme that produces sugars from biomass. In some embodiments, the enzyme used for saccharification can comprise enzymes produced by DSM Food Specialties® B.V. (The Netherlands), such as those directed towards food processing. Any cellulase/hemicellulose enzymes known in the art can be used in enzymatic saccharification processes described herein. The preferred enzyme concentration and time period for the enzymatic hydrolysis is generally recommended by the manufacturer. In various embodiments, the enzyme concentration can range from about 1 to about 10 percent by weight, or about 2 to about 5 percent by weight. In a preferred embodiment, the enzyme concentration can be about 3 percent by weight of the total materials undergoing enzymatic hydrolysis. In various embodiments, significant hydrolysis (i.e., about 50 to about 75 percent conversion of the starting cellulose materials) can be achieved in about 48 hours.

In various embodiments, the residual solids can be removed from the liquid mash through centrifugation, filtration or other means of liquid/solid separation. A centrifuge or other similar equipment can help with solids and liquid separations. See, e.g., the equipment disclosed in U.S. Pat. No. 521,104 to Davis, U.S. Pat. No. 3,168,474 to Stallman et al., U.S. Pat. No. 5,713,826 to West, and U.S. Pat. No. 7,060,017 to Collier, each of which is herein incorporated by reference in its entirety.

In certain embodiments, the separated liquid can be condensed to form a syrup. An evaporator, for example, can be used to condense the liquid product. In certain embodiments, a mechanical vapor recompression (MVR) evaporator can be useful to assist with condensing the syrup. See, e.g., the evaporators and processes disclosed in U.S. Pat. No. 4,303,468 to Laguilharre et al., U.S. Pat. No. 3,396,086 to Starmer, and U.S. Pat. No. 4,530,737 to Ostman; and U.S. Pat. App. Pub. No. 2014/0262730 to Zimmer, each of which is herein incorporated by reference. The concentrated syrup derived from a hydrolyzed tobacco product can comprise at least about 80% glucose by weight, at least about 85% glucose by weight, or at least about 90% glucose by weight. In certain embodiments, the concentrated syrup can comprise about 20% xylose by weight or less, about 15% xylose by weight or less, about 10% xylose by weight or less, or about 5% xylose by weight or less.

In various embodiments, an enzyme can be added to the saccharification process in order to reduce the amount of xylose in the liquid product. The enzyme can remove the hemicellulose before the final saccharification, for example. In various embodiments, the enzyme can be selected from the group consisting of RHYZYME® (produced by American BioSystems®, Inc.), PULPZYME® HC & HC 2500 (produced by NOVOZYMES® A/S), DYADIC® Xylanase (produced by Dyadic® Inc.), and combinations thereof. RhyzymeRHYZYME® is an enzyme with high specificity to hemicellulose, with only small amounts of cellulase activity. PULPZYME® HC & HC 2500 is an enzyme which is very specific to hemicellulose, and again has very little amounts of cellulase activity. DYADIC® Xylanase is an enzyme that has been shown to have high cellulase activity as well as high xylanase activity. The preferred enzyme concentration is generally recommended by the manufacturer.

High fructose tobacco syrup can be produced using commercial immobilized glucose isomerase (e.g., SWEETZYME® type IT produced by NOVOZYMES®). See, e.g., Gaily, M. H., et al. *Production of fructose from highly concentrated date extracts using Saccharomyces cerevisiae.* Biotechnology Letters, 2013, herein incorporated by reference it its entirety. As illustrated at operation 112 of FIG. 1, for example, this isomerization can convert glucose, which is not very sweet, to fructose, the sweetest natural sugar. Glucose isomerase (D-glucose ketoisomerase) causes the isomerization of glucose to fructose. The isomerization of glucose to fructose is part of the glycolysis cycle that converts glucose to pyruvate. The way this is done is to isomerize the aldehyde (hemiacetal) glucose to the ketone (as a hemiacetal) fructose, and make another phosphate ester. The isomerization takes advantage of the ease of breakage of a C—H bond which involves a carbon next to a carbonyl carbon. In the next step, the bond between carbons three and four of fructose is cleaved.

For example, Novo Industries has developed Sweetzyme®, glucose isomerase from *B. coagulans*, for commercial use. The commercial process for production of fructose from glucose became feasible when procedures for immobilization of the enzyme were developed, so that the same batch of enzymes could be used repeatedly. In this immobilized enzyme process, the microorganism carries out a direct isomerization of the glucose. This glucose isomerase is primarily a xylose isomerase, so xylose, or a xylose-containing compound must be added for the induction of the enzyme.

Figure 1B:
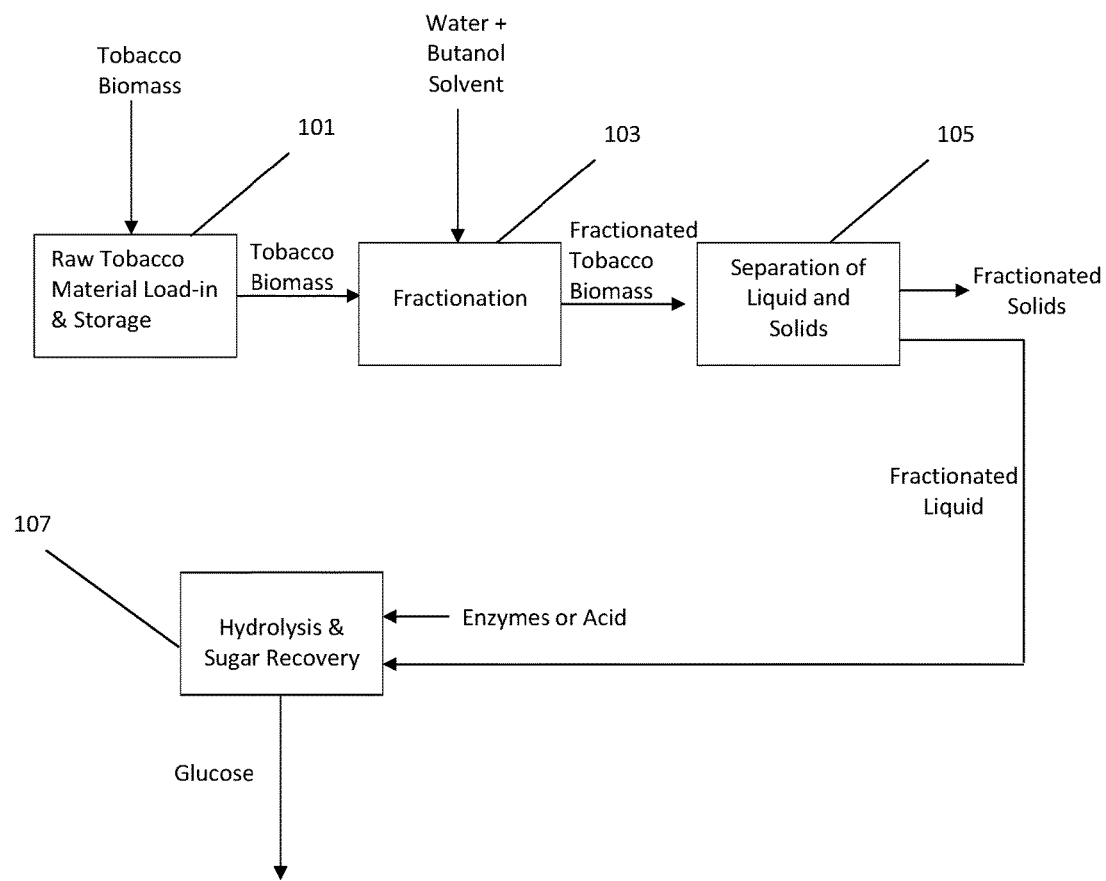
FIG. 1b is a flow chart describing methods of forming cellulosic sugars from tobacco biomass materials.

As illustrated in FIG. 1b, for example, tobacco biomass can alternatively be converted to sugar using an Organosolv process. See, e.g., the process described in U.S. Pat. Appl. Pub. No. 2014/0227161 to Manesh et al., which is herein incorporated by reference. In particular, tobacco biomass can first undergo a fractionation process, as illustrated at operation 103 of FIG. 1b. In certain embodiments, the fractionation process can include adding tobacco materials (dry weight) and a solvent in a solid to liquid ratio of about 1:5 to about 1:10 by weight to a reactor. The solvent can comprise water and butanol, for example, in about a 1:1 ratio by weight. The mixture of the tobacco materials and the solvent can be stirred for about 30 to about 60 mins at an elevated temperature of about 150° C. to about 200° C. (e.g., about 178° C.). An acid can be added to the reaction mixture (e.g., sulfuric acid) in an amount sufficient to drop the pH to about 2.

After fractionation, the liquid and the solids can be separated using any separation method known in the art, as illustrated at operation 105. The liquid can be collected in a separate container where the organic materials and lignin can be separated from water and water soluble materials in two layers. The cellulose (solids) can be centrifuged to collect the adsorbed solvents in the fiber, washed with water and processed for enzymatic hydrolysis to convert the cellulose to tobacco-derived sugars (e.g., glucose), as illustrated at operation 107 and discussed in more detail above. The average cellulose yield can be about 30 wt % of the total dry biomass. The butanol (and other chemicals like furfural and esters) from the liquor can be distilled off to produce high quality lignin. In this process >95% lignin can be recovered from the biomass. This lignin is of high purity with melting properties around 234° C. and soluble in a wide range of organic solvents. In various embodiments, over 80% of the total C5 sugars can be converted to furfural during the fractionation process and collected in the butanol layer. Organic acids from the tobacco feedstock can also be partially captured in the form of esters in the butanol layer.

Nitrogenous Compounds Derived from Tobacco Materials

According to the present invention, amino acids derived from tobacco materials can serve as the tobacco-derived nitrogen source in a pyrazine reaction. Amino acids can be derived from hydrolysis of tobacco-derived protein, as illustrated in FIGS. 2a and 2b, for example.

Figure 2A:
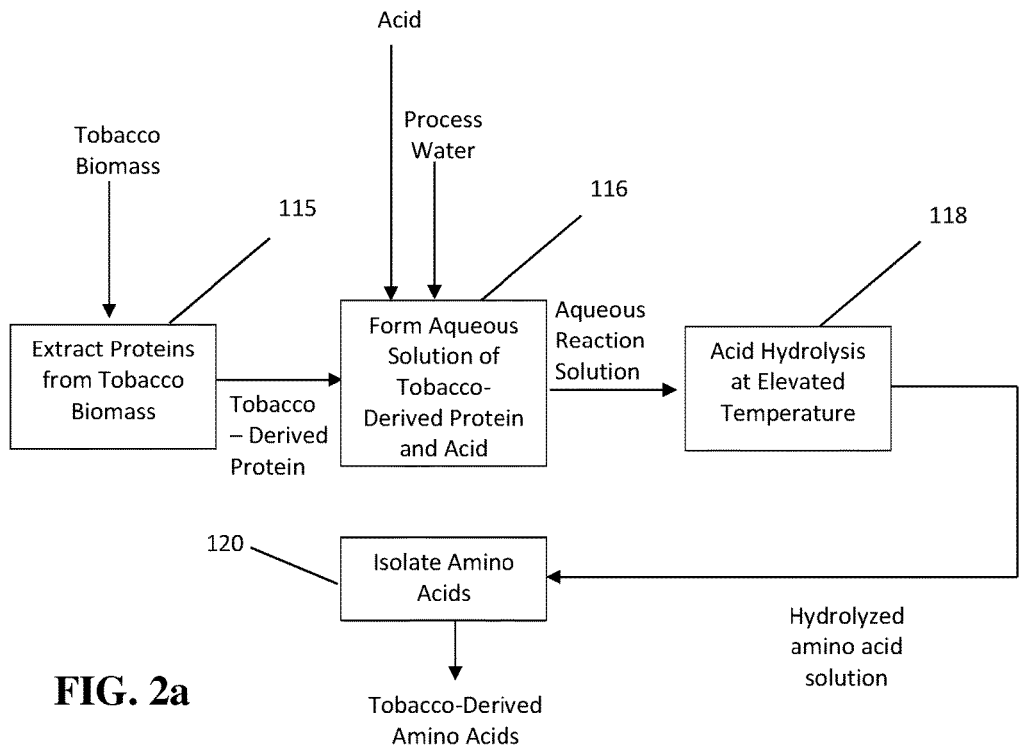
FIG. 2a is a flow chart describing methods of forming amino acids from tobacco biomass materials via acid hydrolysis.
Figure 2B:
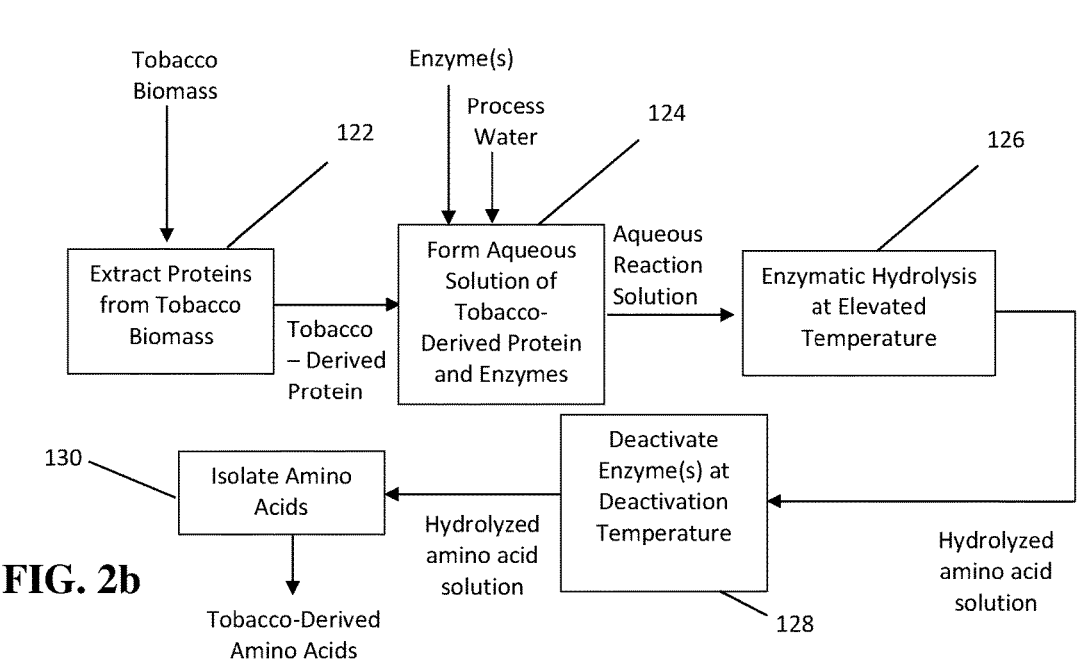
FIG. 2b is a flow chart describing methods of forming amino acids from tobacco biomass materials via enzymatic hydrolysis.

As illustrated at operation 115 of FIG. 2a and at operation 122 of FIG. 2b, for example, a portion or portions of a plant of the *Nicotiana* species can be treated so as to provide one or more components (e.g., proteins) contained therein in a more usable (e.g., more concentrated) form. Various compounds or mixtures of compounds from the *Nicotiana* plant or portions thereof can be extracted and/or isolated by methods such as those described in U.S. Pat. App. Pub. No. 2014/0271952 to Mua et al., for example, which is incorporated by reference in its entirety. As used herein, an "isolated component," or "plant isolate," is a compound or complex mixture of compounds separated from a plant of the *Nicotiana* species or a portion thereof. The isolated component can be a single compound, a homologous mixture of similar compounds (e.g., isomers of a compound), or a heterologous mixture of dissimilar compounds (e.g., a complex mixture of various compounds of different types). See, for example, the description of isolated tobacco components and techniques for isolation in US Pat. Appl. Pub. Nos. 2007/0137663 to Taylor et al.; 2011/0174323 to Coleman, III et al.; 2011/0259353 to Coleman, III et al.; 2012/0141648 to Morton et al.; 2012/0192880 to Dube et al.; 2012/0192882 to Dube et al.; 2012/0272976 to Byrd et al., 2012/0211016 to Byrd, Jr. et al., and 2014/0096780 to Gerardi et al., which are incorporated by reference herein.

Exemplary tobacco plant materials from which proteins can be extracted can be of any part or in any form of a plant of the *Nicotiana* species. The selection of the plant from the *Nicotiana* species can vary; and in particular, the types of tobacco or tobaccos may vary. The *Nicotiana* species can be selected for the content of various compounds that are present therein. For example, plants can be selected on the basis that those plants produce relatively high quantities of one or more of the compounds desired to be isolated therefrom (e.g., proteins). In certain embodiments, plants of the *Nicotiana* species (e.g., *Galpao commun* tobacco) are specifically grown for their abundance of leaf surface compounds.

As described in U.S. Pat. App. Pub. No. 2014/0271952 to Mua et al., which is incorporated herein by reference, protein can be extracted from a biomass such as a plant material (e.g., tobacco). See also, U.S. Pat. No. 4,268,632 to Wildman et al., U.S. Pat. No. 4,340,676 to Bourke; U.S. Pat. No. 4,400,471 to Johal; U.S. Pat. No. 4,588,691 to Johal; and U.S. Pat. No. 6,033,895 to Garger et al., which are incorporated herein by reference. Generally, the water-soluble portion of plant biomass consists of two fractions. One fraction predominantly comprises ribulose-1,5-bisphosphate carboxylase oxygenase (commonly referred to as RuBisCO), whose subunit molecular weight is about 550 kD (commonly referred to as a "Fraction 1 protein" or "F1 protein"). RuBisCO may comprise up to about 25% of the total protein content of a leaf and up to about 10% of the solid matter of a leaf. A second fraction ("Fraction 2 protein" or "F2 protein") generally contains a mixture of proteins and peptides with molecular weights ranging from about 3 kD to about 100 kD and may also contain other compounds including sugars, vitamins, alkaloids, flavors, and amino acids.

Protein consists of long chains of amino acids. Several methods exist to breakdown protein into the constituent amino acids. For example, any form of hydrolysis known in the art can be used to break the tobacco-derived protein into constituent amino acids. In certain embodiments, a salt of a weak acid or a weak base (or both) can be dissolved in water in a hydrolysis process. Acid-base-catalyzed hydrolyses can also be used, for example. In various embodiments, tobacco-derived protein can undergo enzymatic hydrolysis to form amino acids. During hydrolysis, the protein is broken down into smaller peptides, and full hydrolysis breaks down the protein into individual amino acids. Amino acids range in size with molecular weights between 50 and 200. Peptides consist of 2 to 50 amino acids and range in size between 100 and 10,000. Anything larger than that is considered to be a protein. After hydrolysis, the amino acids can be isolated via any method known in the art, such as, but not limited to, ion exchange liquid chromatography (both standard LC and HPLC), gas chromatography combustion IRMS (GC-C-IRMS), hydrophobic chromatography, etc., affinity chromatography, sublimation, etc.

In various embodiments, as illustrated in FIG. 2a for example, acid hydrolysis can be used to breakdown tobacco-derived protein into amino acids. Various acids can be used for acid hydrolysis, as is known in the art. For example, hydrochloric acid (HCl) can be used. As illustrated at operation 116 of FIG. 2a, for example, the acid and the tobacco-derived protein can be in the form of an aqueous solution. As illustrated at operation 118 of FIG. 2a, for example, the aqueous solution can be heated to an elevated temperature during hydrolysis. For example, the aqueous solution can be heated to about 160° C. or higher, about 180° C. or higher, or about 200° C. or higher. The time for hydrolysis can vary depending on the protein and the acid used. In some embodiments, the aqueous solution can be heated to the elevated temperature with about a 10 to about a 20 minute (e.g., 15 minute) ramp time and then held at the elevated temperature for about 10 to about 20 minutes (e.g., about 15 minutes). These times are not intended to be limiting. As illustrated at operation 120 of FIG. 2a, for example, tobacco-derived amino acids can be isolated from the hydrolyzed solution via methods known in the art, such as, but not limited to, ion exchange liquid chromatography (both standard LC and HPLC), gas chromatography combustion IRMS (GC-C-IRMS), hydrophobic chromatography, etc., affinity chromatography, sublimation, etc.

In various embodiments, as illustrated in FIG. 2b for example, enzymatic hydrolysis can be used to breakdown tobacco-derived protein into amino acids. Various types of enzymes can be used. Endoproteases cleave from the middle of the peptides, and exoproteases cleave amino acids off of the ends of the peptides. For example, MAXAZYME® NNP DS (available from DSM Food Specialties® in Brenntag, NV), ACCELERZYME® CPG (available from DSM Food Specialties® in Brenntag, NV), and VALIDASE® FP Concentrate (available from Valley Research®, South Bend, Ind.) represent enzymes that can be used for enzymatic hydrolysis of tobacco-derived protein. MAXAZYME® NNP DS is an endoprotease and ACCELERZYME® CPG and VALIDASE® FP Concentrate are exoproteases. The amount of enzyme used is typically recommended by the manufacturer. For example, in a preferred embodiment, approximately 1 g of F1 tobacco-derived protein in about 100 mL of water can by hydrolyzed with about 50 mg of MAXAZYME® NNP DS and about 50 mg of VALIDASE® FP Concentrate at approximately 50° C. for about 20 hours to obtain approximately 39% amino acids by weight of the hydrolyzed product.

In various embodiments of enzymatic hydrolysis, the tobacco-derived protein and the enzymes used can be diluted in deionized water, as illustrated at operation 124 of FIG. 2b for example. The pH of the aqueous solution can be adjusted depending on the recommended pH of the specific enzyme used. For example, MAXAZYME® NNP DS and VALIDASE® FP Concentrate are active at neutral pH, and ACCELERZYME® CPG is active at an acidic pH.

As illustrated at operation 126 of FIG. 2b for example, the aqueous solution of the tobacco-derived protein and the enzyme(s) can be heated to an activation temperature for hydrolysis. For example, the aqueous solution can be heated to about 40° C. or higher, to about 50° C. or higher, or to about 60° C. or higher. The activation temperature can depend on the enzyme(s) used and will typically be recommended by the manufacturer. The aqueous solution can be held at the activation temperature for about 4 hours or longer, about 15 hours or longer, or about 20 hours or longer. As illustrated at operation 128 of FIG. 2b, for example, once hydrolysis is complete, the aqueous solution can be heated to a deactivation temperature, which is higher than the activation temperature, to deactivate the enzyme(s). For example, the deactivation temperature can be about 75° C. or higher, to about 85° C. or higher, or to about 95° C. or higher. The deactivation temperature can depend on the enzyme(s) used and will typically be recommended by the manufacturer. The aqueous solution can be held at the deactivation temperature for about 5 minutes or longer, about 10 minutes or longer, about 15 minutes or longer, or about 20 minutes or longer. As illustrated at operation 130 of FIG. 2b, for example, tobacco-derived amino acids can be isolated from the hydrolyzed solution via methods known in the art, such as, but not limited to, ion exchange liquid chromatography (both standard LC and HPLC), gas chromatography combustion IRMS (GC-C-IRMS), hydrophobic chromatography, etc., affinity chromatography, sublimation, etc.

Figure 5A:
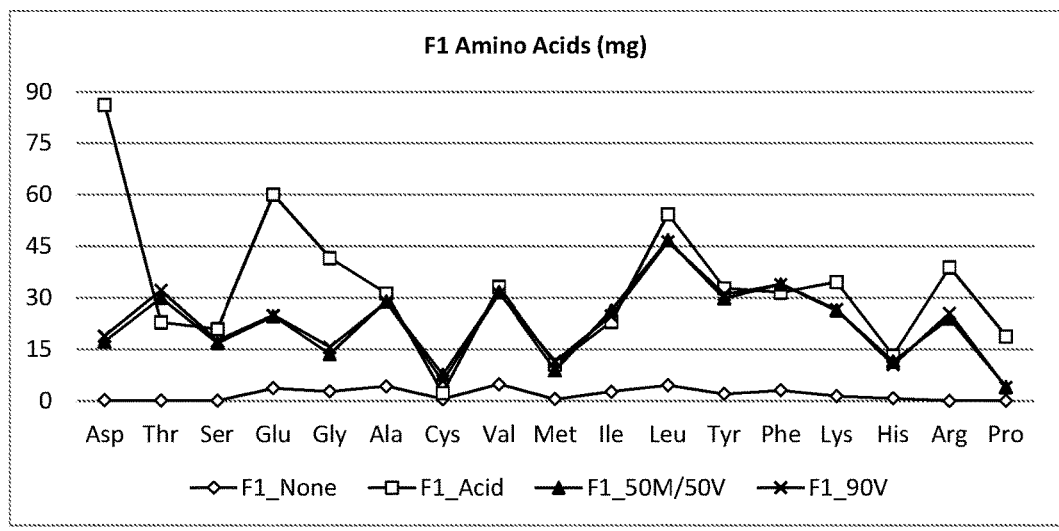
FIG. 5a is a graph illustrating the amino acid distribution (mg) based on the hydrolysis conditions used on F1 type tobacco-derived protein.
Figure 5B:
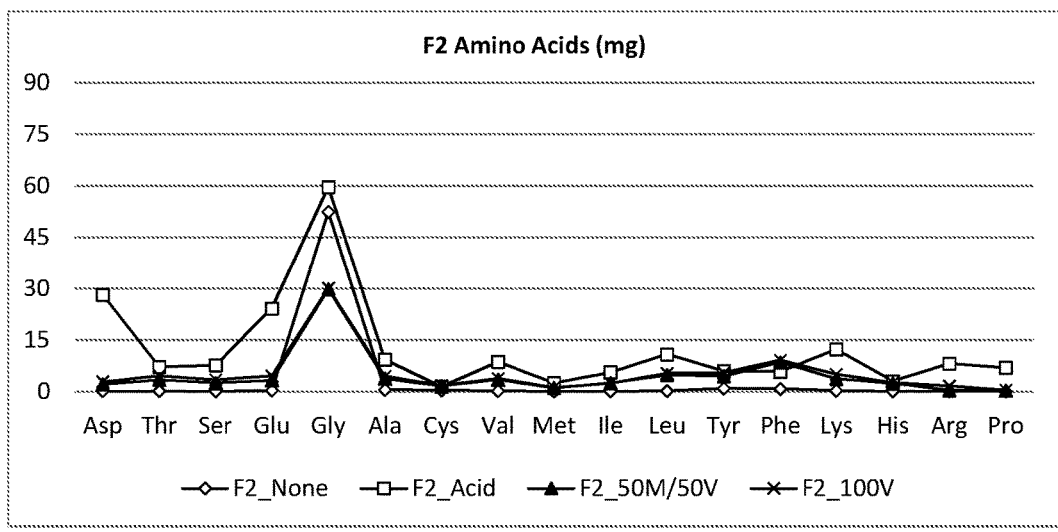
FIG. 5b is a graph illustrating the amino acid distribution (mg) based on the hydrolysis conditions used on F2 type tobacco-derived protein.
Figure 6A:
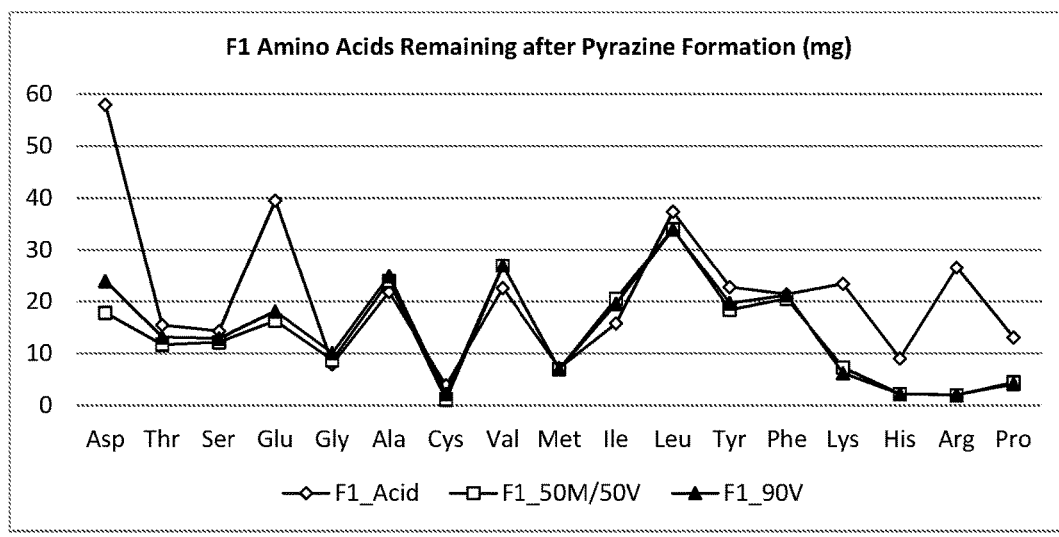
FIG. 6a is a graph illustrating the amino acids (mg), derived from an F1 type tobacco-derived protein, that remain following a reaction to form pyrazines.
Figure 6B:
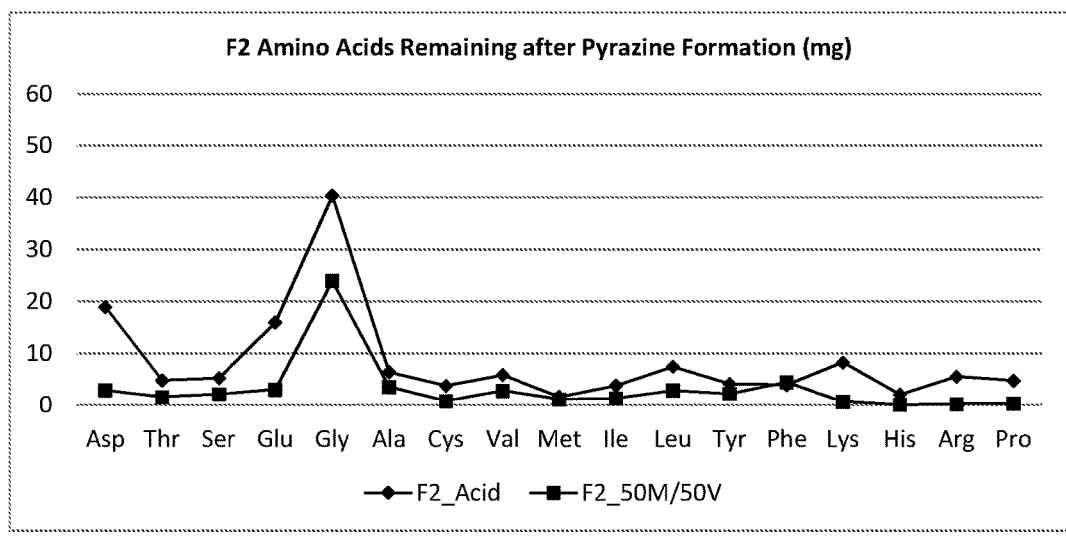
FIG. 6b is a graph illustrating the amino acids (mg), derived from an F2 type tobacco-derived protein, that remain following a reaction to form pyrazines.
Figure 7A:
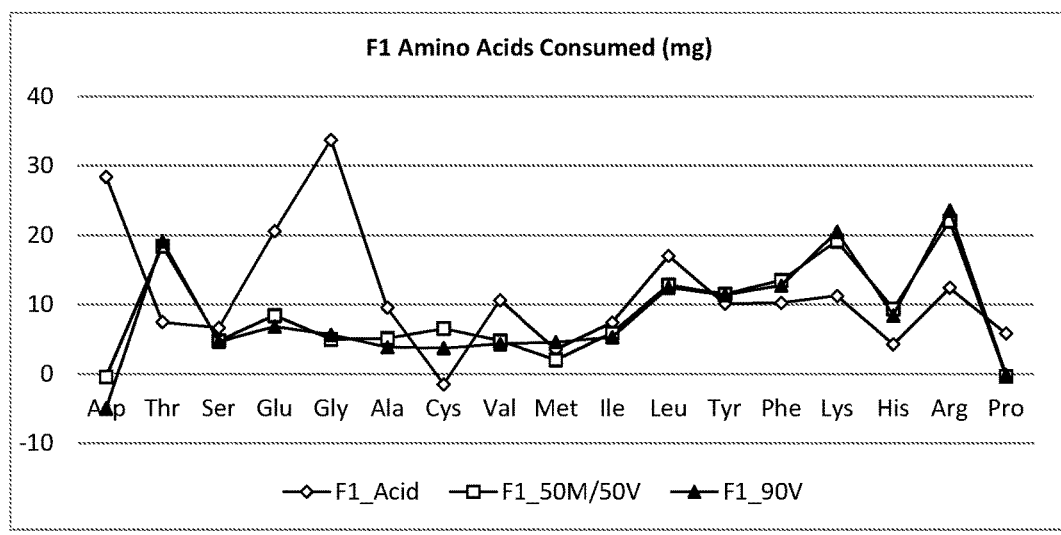
FIG. 7a is a graph illustrating the amino acids (mg), derived from an F1 type tobacco-derived protein, that are consumed during a reaction to form pyrazines.
Figure 7B:
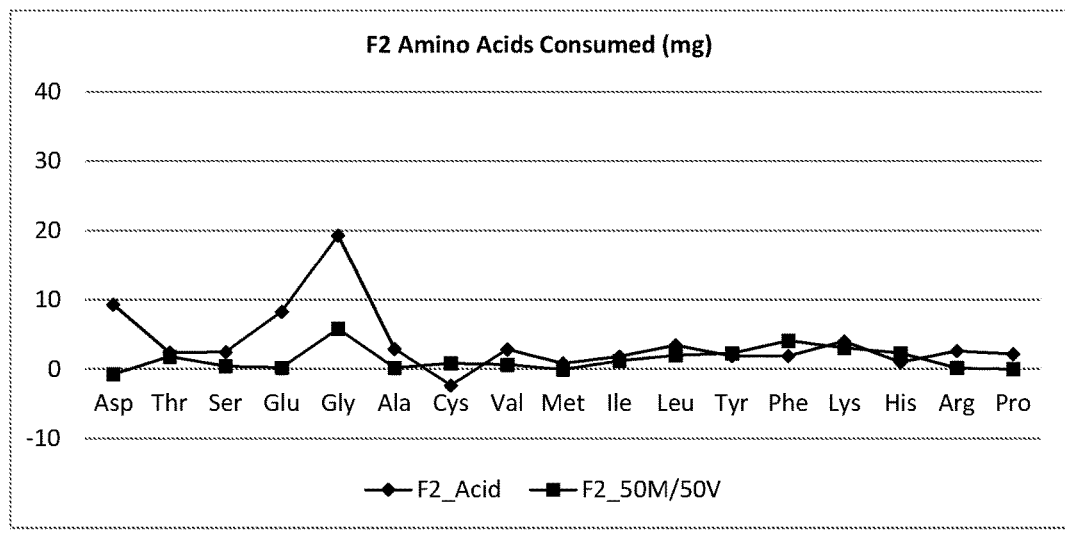
FIG. 7b is a graph illustrating the amino acids (mg), derived from an F2 type tobacco-derived protein, that are consumed during a reaction to form pyrazines.

As illustrated in FIGS. 5a and 5b, for example, various amino acids can be derived from acid or enzymatic hydrolysis of tobacco-derived protein. For example, the amino acids derived from hydrolysis of tobacco-derived protein can include aspartic acid (Asp), threonine (Thr), serine (Ser), glutamic acid (Glu), glycine (Gly), alanine (Ala), cysteine (Cys), valine (Val), methionine (Met), isoleucine (Ile), leucine (Leu), tyrosine (Tyr), phenylalanine (Phe), lysine (Lys), histidine (His), arginine (Arg), proline (Pro), and combinations thereof. Different amino acids can be favored depending on the type of protein and hydrolysis conditions used. Both F1 and F2 tobacco-derived protein can serve as a source of amino acids.

Ammonium Ions Derived from Tobacco Materials

Ammonium ($NH_4^+$) facilitate the reaction of sugars and nitrogenous compounds to form pyrazines. This has been demonstrated using diammonium phosphate (DAP), for example. See, e.g., On the synthesis and characteristics of aqueous formulations rich in pyrazines, in Flavor Fragrance and Odor Analysis, Second Edition, Ray Marsili, ed., Chapter 7, pp 135-182, CRC Press, Boca Raton, 2012; which is herein incorporated by reference. It has also been shown that ammonium hydroxide also works to facilitate the reaction.

Ammonium ions can be derived from a plant of the *Nicotiana* species. In certain embodiments, the ammonium ions can be in the form of ammonium hydroxide, for example. One possible way to produce ammonium hydroxide can be via the electrochemical reduction of potassium nitrate found in biomass derived from a plant of the *Nicotiana* species. It is well known in the art that potassium nitrate is very soluble in water at elevated temperatures, but has a very low solubility at lower temperatures. It has been discovered that burley stems have a relatively high concentration of potassium nitrate (around about 10% on a dry weight basis). Accordingly, methods of extracting potassium nitrate from tobacco materials described herein focus on using burley stems as the starting tobacco material, but the invention is not limited to such embodiments. Other *Nicotiana* species and other parts of the plant can be used in the methods described herein.

Figure 3:
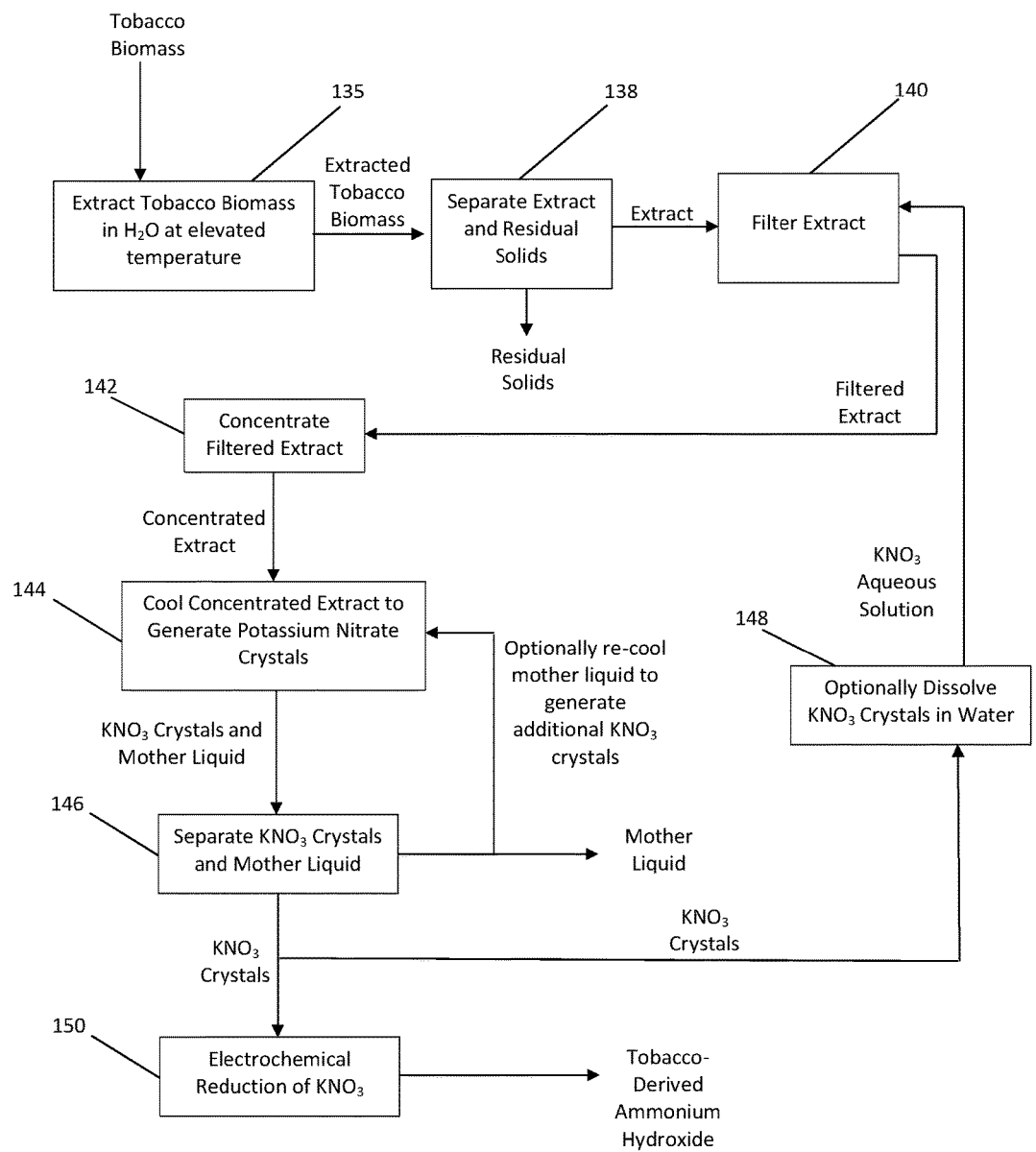
FIG. 3 is a flow chart describing methods of forming ammonium hydroxide from tobacco biomass materials.

In various embodiments of the present invention, tobacco biomass (e.g., burley stems) can undergo a denitration process to produce potassium nitrate, as illustrated in FIG. 3, for example. At operation 135, for example, tobacco biomass (e.g., burley stems) can be extracted in water at an elevated extraction temperature. In various embodiments, the tobacco biomass can be extracted in about a 10:1 ratio to about a 1:10 ratio, or about a 5:1 ratio to about a 1:5 ratio of water to tobacco biomass. In a preferred embodiment, the tobacco biomass is extracted in about a 10:1 ratio of water to tobacco biomass. In various embodiments, the extraction temperature can be about 120° C. or higher, about 150° C. or higher, about 160° C. or higher, or about 180° C. or higher. In a preferred embodiment, the extraction temperature can be about 160° C., for example. In various embodiments, the tobacco biomass can be extracted for at least about 1 hour, at least about 2 hours, at least about 4 hours, or at least about 24 hours.

As illustrated at operation 138 of FIG. 3, for example, the extract can be separated from the fibrous tobacco solids by centrifugation and passing through a mesh screen on a shaker, or via other means known in the art. A centrifuge or other similar equipment can help with solids and liquid separations. See, e.g., the equipment disclosed in U.S. Pat. No. 521,104 to Davis, U.S. Pat. No. 3,168,474 to Stallman et al., U.S. Pat. No. 5,713,826 to West, and U.S. Pat. No. 7,060,017 to Collier, each of which is herein incorporated by reference in its entirety. Following the initial separation, the extract can have about a 5% or less solids content, or about a 2% or less solids content, for example.

As illustrated at operation 140 of FIG. 3, for example, the initially separated extract can be filtered to form a filtered extract. The process of filtration can comprise passing the liquid through one or more filter screens to remove selected sizes of particulate matter. As described above, screens may be, for example, stationary, vibrating, rotary, or any combination thereof. For example, in some embodiments, the extract can be pumped through a sock filter before being passed through a filter bag installed in a Sanborn centrifuge.

As illustrated at operation 142 of FIG. 3, for example, the filtered extract can be concentrated. An evaporator, for example, can be used to condense the filtered extract. In certain embodiments, a mechanical vapor recompression (MVR) evaporator can be useful to assist with condensing the syrup. See, e.g., the evaporators and processes disclosed in U.S. Pat. No. 4,303,468 to Laguilharre et al., U.S. Pat. No. 3,396,086 to Starmer, and U.S. Pat. No. 4,530,737 to Ostman; and U.S. Pat. App. Pub. No. 2014/0262730 to Zimmer, each of which is herein incorporated by reference. In various embodiments, the filtered extract can be concentrated to about 25% or less, about 20% or less, or about 15% or less solids content. In some embodiments of the present invention, the concentrated extract can undergo one or more additional filtration steps and one or more additional concentration steps. Following additional filtration and concentration processes, the solids concentration of the concentrated extract can be raised to about 50% or less, about 40% or less, or about 30% or less.

As illustrated at operation 144 of FIG. 3, for example, the concentrated extract can be chilled to begin potassium nitrate crystal generation. In some embodiments, the concentrated extract can be chilled to about −5° C. to about 5° C. for about 12 hours or longer, about 24 hours or longer, or about 36 hours or longer. In certain embodiments, the concentrated extract can be allowed to cool to room temperature before chilling the concentrated extract at the lower crystal generation temperature. Following cooling, the potassium nitrate crystals and the mother liquid can be separated through any means known in the art, as illustrated at operation 146 of FIG. 3, for example. In certain embodiments, a mesh bag or similar filtration device can be used to separate the potassium nitrate crystals and the mother liquid. In some embodiments, following separation, the separated mother liquid can be placed back into a cooler for about 12 hours or longer, about 24 hours or longer, or about 36 hours or longer to generate a second crop of potassium nitrate crystals. This process can be repeated until no additional potassium nitrate crystals are generated.

As illustrated at operation 148 of FIG. 3, for example, the potassium nitrate crystals, which can contain trapped tobacco solids, can optionally be purified (i.e., trapped tobacco solids can be at least partially removed). For example, the potassium nitrate crystals can be dissolved in water at about a 1:2 to about a 2:1 ratio and heated until the crystals dissolve. In a preferred embodiment, the potassium nitrate crystals can be dissolved in water at about a 1:1 ratio of crystals to water. The resulting solution can then undergo the filtration, concentration, crystal generation, and separation processes, as illustrated at operations 140, 142, 144 and 146 of FIG. 3, for example. This cycle can be repeated as necessary until a desired level of purity is reached.

As illustrated at operation 150 of FIG. 3, for example, the potassium nitrate crystals can undergo electrochemical reduction to form tobacco-derived ammonium hydroxide. Although there have been research efforts reported in the literature to study the electrochemical reduction of nitrate, most of these have been concerned with eliminating nitrate from drinking water, for example, rather than the production of ammonia. See, e.g., Electrochemical reduction of nitrate in weakly alkaline solutions; K. Bouzek, M. Paidar, A. Sadílková, H. Bergmann; Journal of Applied Electrochemistry, November 2001, Volume 31, Issue 11, pp 1185-1193; Electrocatalytic activity of copper alloys for Nitrate reduction in a weakly alkaline solution Part 1: Copper-zinc; Z. Mácová, K. Bouzek; Journal of Applied Electrochemistry, December 2005, Volume 35, Issue 12, pp 1203-1211; and Electrochemical reduction of nitrates and nitrites in alkaline nuclear waste solutions, J. D. Genders, D. Hartsough, D. T. Hobbs; Journal of Applied Electrochemistry, January 1996, Volume 26, Issue 1, pp 1-9; each of which is herein incorporated by reference. However, ammonia can also be produced from the reduction. There are several possible reactions that can occur at the cathode, which are as follows:

$$NO_3^- + H_2O + 2e^- = NO_2^- + 2OH^-$$

$$2NO_2^- + 3H_2O + 4e^- = N_2O + OH^-$$

$$NO_2^- + 5H_2O + 6e^- = NH_3 + 7OH^-$$

$$NO_3^- + 6H_2O + 8e^- = NH_3 + 9OH^-$$

$$NO_3^- + 3H_2O + 5e^- = \tfrac{1}{2}N_2 + OH^-$$

$$H_2O + e^- = \tfrac{1}{2}H_2 + OH^-$$

The reaction pathways and efficiency for ammonia production can be highly dependent on the electrode materials chosen. For example, in some embodiments, the best yields of ammonia can be obtained with the use of high surface area electrodes comprising graphite and/or nickel. Furthermore, the use of high surface area electrodes can facilitate the use of high current densities (i.e. high rates of reaction) and near complete reduction of the nitrate.

Formation of Pyrazines from Tobacco-Derived Reactants

Pyrazines display many different flavor profiles, including, but not limited to, roasted, toasted and nutty notes. For example, pyrazines with cyclopentyl derivatives are known for their positive sensory attributes at very low levels, ppb. Selected pyrrolizine and pyrrolidine compounds are known for their woody, smoky and weak amine sensory characteristics, while others having amine-type notes are reminiscent of ammonia. Maltoxazine, for example, is found to have zero odor potency.

Figure 4:
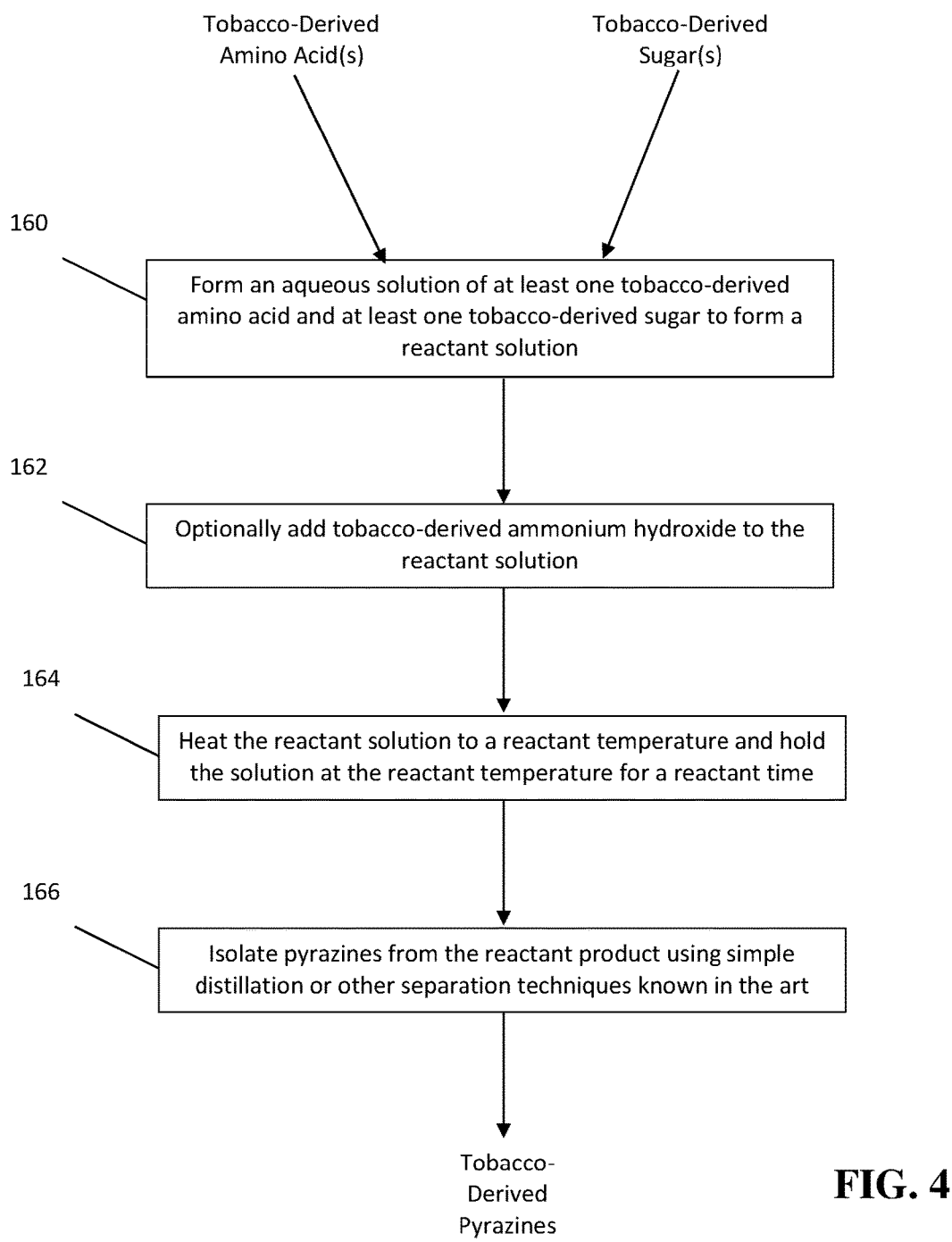
FIG. 4 is a flow chart describing methods of forming pyrazines from reactants derived from a harvested plant of the *Nicotiana* species.

As illustrated in FIG. 4, for example, heated formulations comprising amino acids and sugars can produce pyrazines. See, e.g., U.S. Pat. Pub. No. 2010/0037903 to Coleman III et al.; and Coleman III, On the synthesis and characteristics of aqueous formulations rich in pyrazines, in Flavor Fragrance and Odor Analysis, Second Edition, Ray Marsili, ed., Chapter 7, pp 135-182, CRC Press®, Boca Raton, 2012; which are herein incorporated by reference in their entireties. As described herein, it is discovered that both the amino acid and the sugar components of the pyrazine reaction can be derived from a plant of the *Nicotiana* species. It is further discovered that addition of aqueous ammonium hydroxide (NH$_4$OH) to the aqueous reaction media containing at least one amino acid and at least one sugar can result in formulations very rich in pyrazines, >500 µg/mL, >1000 µg/mL, >1500 µg/mL, or >2000 µg/mL, for example. As described above, ammonium hydroxide can also be derived from a plant of the *Nicotiana* species. Accordingly, various embodiments of the methods and products of the present invention provide pyrazines derived entirely from a plant of the *Nicotiana* species.

Different sugars and amino acids affect the types of pyrazines formed. See, e.g., Coleman and Steichen, 2006, Sugar and selected amino acid influences on the structure of pyrazines in microwave heat treated formulations, J. Sci. Food Agric., 86, 380-391, which is herein incorporated by reference in its entirety. For example, leucine and valine produce more branched pyrazines with highly substituted subchains and lower odor thresholds. Highly substituted pyrazines are relatively more potent than pyrazines that are not as branched, and therefore can be desirable in some applications. The substitution in the pyrazine can be a result of the amino acid used in the reaction. Therefore, it can be advantageous to select amino acids with branching, highly substituted subchains. With regard to sugars, rhamnose can be an ideal sugar for pyrazine formation, followed by fructose and then glucose.

Pyrazine rich solutions can be prepared in various ways. For example, one method can involve microwave heat treatment of a solution comprising at least one amino acid and at least one sugar. As illustrated at operation 160 of FIG. 4, for example, an aqueous reactant solution comprising at least one tobacco-derived amino acid and at least one tobacco-derived sugar can be formed. As illustrated at operation 164 of FIG. 4, for example, the reactant solution can be heated to a reactant temperature and held at the reactant temperature for a reactant time which is sufficient to allow the reactants to undergo a reaction to form pyrazines.

Increased reaction time and temperature can produce increased pyrazines yield up to the point where a black TAR substance is produced. Reaction temperature can be about 30° C. or greater, about 90° C. or greater, about 100° C. or greater, or about 120° C. or greater, for example. In some embodiments, the reaction temperature can be about 90° C. to about 150° C., or about 120° C. to about 140° C. Reaction time can be about 30 mins or greater, 60 mins or greater, about 90 mins or greater, or about 120 mins or greater, for example. In various embodiments, the reaction time can be about 30 mins to about 150 mins, or about 60 mins to about 120 mins.

Increasing the pH of the reactant solution can also result in increased amounts of pyrazines. A favored pH range can be about 7.5 to about 10.5 (e.g., about 10.0), or to about 8.5 to about 9.5 (e.g., about 9.5). In some embodiments, the pH of the reactant solution can be about 8.0 or greater, about 8.5 or greater, about 9.0 or greater or about 10.0 or greater. A small addition of NaOH or KOH, for example, can be used to increase the pH of the reactant solution.

In various embodiments of the present invention, as illustrated at operation 162 of FIG. 4 for example, the addition of NH$_4$OH to the amino acid/sugar reactant solution can increase the yield of pyrazines. The NH$_4$OH/sugar weight ratio can have a dramatic influence on the yield of pyrazines. For example, a mole ratio of sugar to NH$_4$OH of about 5:1, about 2.5:1, about 2:1, or about 1.5:1, followed by heat treatment can produce formulations rich in pyrazines. In some embodiments, aqueous NH$_4$OH can slowly be added into the amino acid/sugar solution over the course of the reaction.

As illustrated at operation 166 of FIG. 4, for example, following the reaction, tobacco-derived pyrazines can be isolated from the reactant product using simple distillation, rotary evaporation, or other separation techniques known in the art. In certain embodiments, rotary evaporation can be a preferred isolation technique in a scaled up process of deriving tobacco-derived pyrazines.

As illustrated in the Examples below, various pyrazines can be derived from tobacco materials. For example, the most abundant groups of pyrazines produced from tobacco-derived reactants can include C1 and C2 pyrazines. These can include pyrazine, 2-methylpyrazine, 2,6-dimethylpyrazine and 2-ethylpyrazine, for example. Pyrazines that can be produced from tobacco-derived reactants include, but are not limited to, pyrazine, 2-methylpyrazine, 2,5-dimethylpyrazine, 2,6-dimethylpyrazine, 2-ethylpyrazine, 2,3-dimethylpyrazine, 2,3,5-trimethylpyrazine, 2-ethyl-6-methylpyrazine, 2-ethyl-5-methylpyrazine, 2-ethyl-3-methylpyrazine, vinylpyrazine, 2-ethyl-3,6-dimethylpyrazine, 2-ethyl-3,5-dimethylpyrazine, 2-methyl-6-vinylpyrazine, 2,6-diethyl-3-methylpyrazine, 2-isoamylpyrazine, 2-isoamyl-6-methylpyrazine, 2-phenylethylpyrazine, and combinations thereof.

Uses of Tobacco-Derived Pyrazines in Tobacco Products

As described above, pyrazines generated according to the present invention can be useful as components (e.g., flavorants) incorporated into tobacco products, for example. The tobacco product to which the materials of the invention are added can vary, and can include any product configured or adapted to deliver tobacco or some component thereof to the user of the product. Exemplary tobacco products include smoking articles (e.g., cigarettes), smokeless tobacco products, and aerosol-generating devices that contain a tobacco material or other plant material that is not combusted during use.

Figure 8:
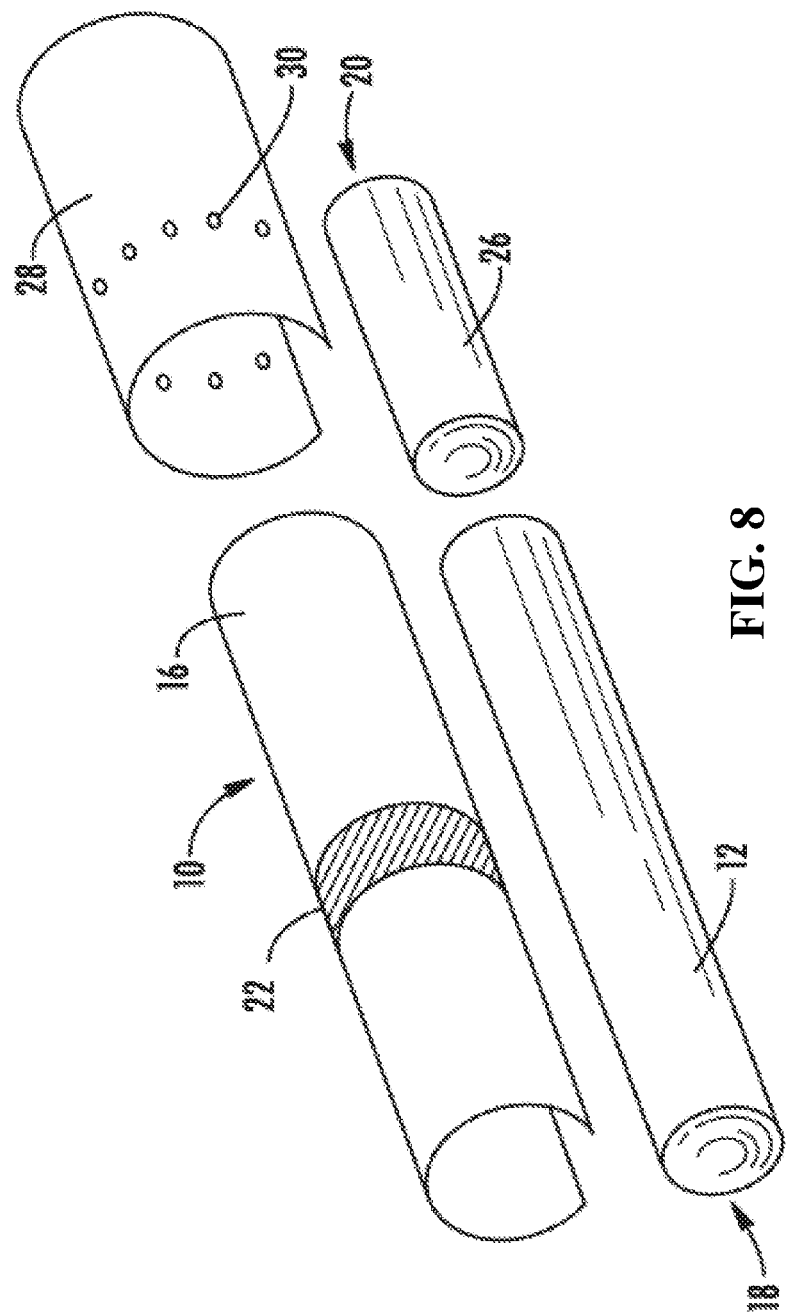
FIG. 8 is an exploded perspective view of a smoking article having the form of a cigarette, showing the smokable material, the wrapping material components, and the filter element of the cigarette.

In various embodiments of the present invention, tobacco-derived pyrazines can be incorporated into smoking articles in the form of a flavorant in a tobacco composition and/or in a filter element of a smoking article. For example, tobacco-derived pyrazines can be incorporated into a top dressing or casing of a tobacco product. Referring to FIG. 8, there is shown a smoking article 10 in the form of a cigarette and possessing certain representative components of a smoking article that can contain products derived from the cellulosic sugar materials of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough. A plug wrap 28 enwraps the filter element and a tipping material (not shown) enwraps the plug wrap and a portion of the outer wrapping material 16 of the rod 12, thereby securing the rod to the filter element 26.

The filter element of the invention typically comprises multiple longitudinally extending segments. Each segment can have varying properties and may include various materials capable of filtration or adsorption of particulate matter and/or vapor phase compounds. Typically, the filter element of the invention includes 2 to 6 segments, frequently 2 to 4 segments. In one preferred embodiment, the filter element includes a mouth end segment, a tobacco end segment and a compartment therebetween. This filter arrangement is sometimes referred to as a "compartment filter" or a "plug/space/plug" filter. The compartment may be divided into two or more compartments as described in greater detail below.

In various embodiments, the filter element can comprise an adsorbent in the form of an activated carbon material, wherein the activated carbon is capable of removing at least one gas phase component of mainstream smoke is incorporated into the filter element. In certain embodiments, the filter element 26 can include ventilation holes 30 that extend through the tipping paper (not shown) and the plug wrap 28 and, thus, provide air dilution of mainstream smoke. The ventilation holes 30 may be configured as a single line of perforations extending circumferentially around the filter element 26 or may comprise several lines of perforations. As would be understood, the exact count and size of the ventilation holes 30 will vary depending on the desired level of air dilution.

Figure 9:
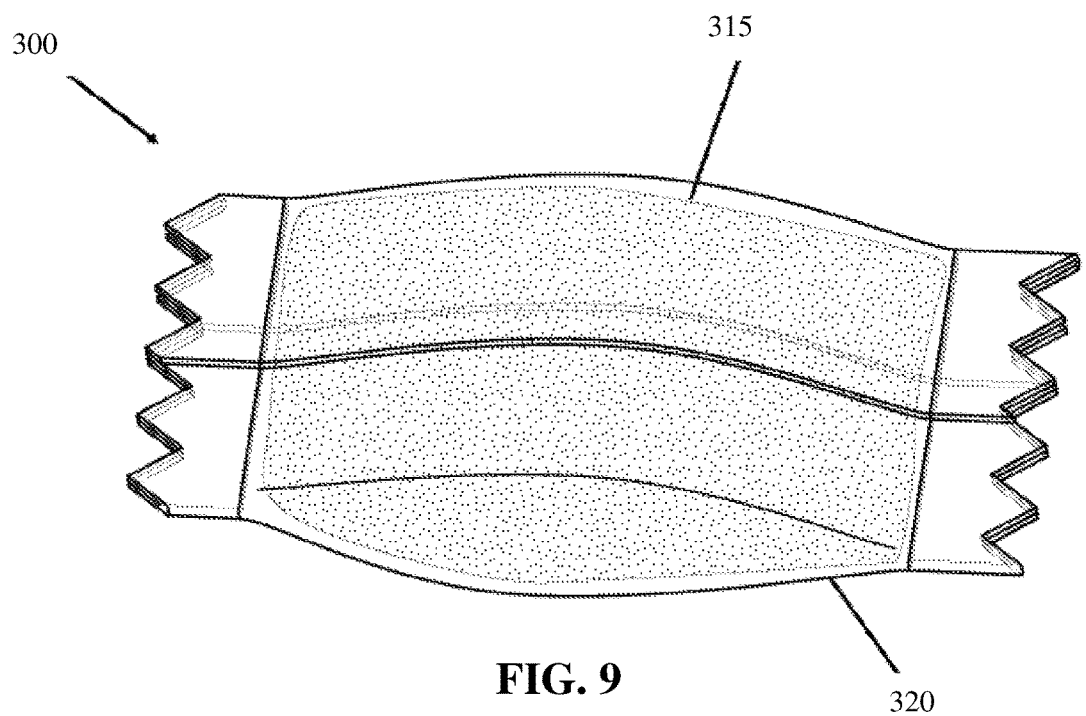
FIG. 9 is a top view of a smokeless tobacco product embodiment, taken across the width of the product, showing an outer pouch filled with a tobacco material.

In various embodiments of the present invention, tobacco-derived pyrazines can be incorporated into smokeless tobacco products in the form of a flavorant in a smokeless tobacco formulation. The form of the smokeless tobacco product of the invention can vary. In one particular embodiment, the product is in the form of a snus-type product containing a particulate tobacco material and a flavorant comprising a tobacco-derived pyrazine. Manners and methods for formulating snus-type tobacco formulations will be apparent to those skilled in the art of snus tobacco product production. For example, as illustrated in FIG. 9, an exemplary pouched product 300 can comprise an outer water-permeable container 320 in the form of a pouch which contains a particulate mixture 315 adapted for oral use. The orientation, size, and type of outer water-permeable pouch and the type and nature of the composition adapted for oral use that are illustrated herein are not construed as limiting thereof.

In various embodiments, a moisture-permeable packet or pouch can act as a container for use of the composition within. The composition/construction of such packets or pouches, such as the container pouch 320 in the embodiment illustrated in FIG. 9, may be varied as noted herein. For example, suitable packets, pouches or containers of the type used for the manufacture of smokeless tobacco products, which can be modified according to the present invention, are available under the tradenames CATCHDRY®, ETTAN®, GENERAL®, GRANIT®, GOTEBORGS RAPE®, GROVSNUS WHITE®, METROPOL KAKTUS®, MOCCA® Anis, MOCCA® Mint, MOCCA® Wintergreen, KICKS®, PROBE®, PRINCE®, SKRUF® and TREANKRARE®. A pouch type of product similar in shape and form to various embodiments of a pouched product described herein is commercially available as ZONNIC® (distributed by NICONOVUM® AB). Additionally, pouch type products generally similar in shape and form to various embodiments of a pouched product are set forth as snuff bag compositions E-J in Example 1 of PCT WO 2007/104573 to Axelsson et al., which is incorporated herein by reference, which are produced using excipient ingredients and processing conditions that can be used to manufacture pouched products as described herein.

The amount of material contained within each pouch may vary. In smaller embodiments, the dry weight of the material within each pouch is at least about 50 mg to about 150 mg. For a larger embodiment, the dry weight of the material within each pouch preferably does not exceed about 300 mg to about 500 mg.

In some embodiments, each pouch/container can have disposed therein a flavor agent member, as described in greater detail in U.S. Pat. No. 7,861,728 to Holton, Jr. et al., which is incorporated herein by reference. The flavor agent member can comprise a flavorant comprising a pyrazine derived from tobacco materials, as discussed above. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

In various embodiments, the outer water-permeable pouch can comprise PLA or other pouch materials known in the art. Descriptions of various components of snus types of products and components thereof also are set forth in US Pat. App. Pub. No. 2004/0118422 to Lundin et al., which is incorporated herein by reference. See, also, for example, U.S. Pat. No. 4,607,479 to Linden; U.S. Pat. No. 4,631,899 to Nielsen; U.S. Pat. No. 5,346,734 to Wydick et al.; and U.S. Pat. No. 6,162,516 to Derr, and US Pat. Pub. No. 2005/0061339 to Hansson et al.; each of which is incorporated herein by reference. See, also, the types of pouches set forth in U.S. Pat. No. 5,167,244 to Kjerstad, which is incorporated herein by reference. Snus types of products can be manufactured using equipment such as that available as SB 51-1/T, SBL 50 and SB 53-2/T from MERZ VERPACKUNGMASCHINEN® GmBH. Snus pouches can be provided as individual pouches, or a plurality of pouches (e.g., 2, 4, 5, 10, 12, 15, 20, 25 or 30 pouches) can connected or linked together (e.g., in an end-to-end manner) such that a single pouch or individual portion can be readily removed for use from a one-piece strand or matrix of pouches.

The invention is not limited to snus-type smokeless tobacco products. For example, the mixture of tobacco material and flavorants comprising at least one tobacco-derived pyrazine can also be incorporated into various smokeless tobacco forms such as loose moist snuff, loose dry snuff, chewing tobacco, pelletized tobacco pieces, extruded tobacco strips or pieces, finely divided or milled agglomerates of powdered pieces and components, flake-like pieces (e.g., that can be formed by agglomerating tobacco formulation components in a fluidized bed), molded tobacco pieces (e.g., formed in the general shape of a coin, cylinder, bean, cube, or the like), pieces of tobacco-containing gum, products incorporating mixtures of edible material combined with tobacco pieces and/or tobacco extract, products incorporating tobacco (e.g., in the form of tobacco extract) carried by a solid inedible substrate, and the like. For example, the smokeless tobacco product can have the form of compressed tobacco pellets, multi-layered extruded pieces, extruded or formed rods or sticks, compositions having one type of tobacco formulation surrounded by a different type of tobacco formulation, rolls of tape-like films, readily water-dissolvable or water-dispersible films or strips (see, for example, US Pat. Appl. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtoniam fluid or a thixotropic fluid incorporating tobacco of some form).

In some embodiments, smokeless tobacco products of the invention can have the form of a lozenge, tablet, microtab, or other tablet-type product. See, for example, the types of lozenge formulations and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference.

Depending on the type of smokeless tobacco product being processed, the tobacco product can include one or more additional components in addition to the tobacco material and the flavorants comprising at least one pyrazine derived from tobacco materials. For example, the tobacco material and the tobacco-derived flavorants can be processed, blended, formulated, combined and/or mixed with other materials or ingredients, such as other tobacco materials or flavorants, fillers, binders, pH adjusters, buffering agents, salts, sweeteners, colorants, disintegration aids, humectants, and preservatives (any of which may be an encapsulated ingredient). See, for example, those representative components, combination of components, relative amounts of those components and ingredients relative to tobacco, and manners and methods for employing those components, set forth in US Pat. Pub. Nos. 2011/0315154 to Mua et al. and 2007/0062549 to Holton, Jr. et al. and U.S. Pat. No. 7,861,728 to Holton, Jr. et al., each of which is incorporated herein by reference.

In various embodiments, at least one pyrazine derived from tobacco materials can be incorporated into smokeless tobacco products in the form of a flavorant in an electronic smoking article. There have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. Pub. Nos. 2013/0255702 to Griffith Jr. et al., 2014/0000638 to Sebastian et al., 2014/0060554 to Collett et al., 2014/0096781 to Sears et al., 2014/0096782 to Ampolini et al., and 2015/0059780 to Davis et al., which are incorporated herein by reference in their entirety.

Figure 10:
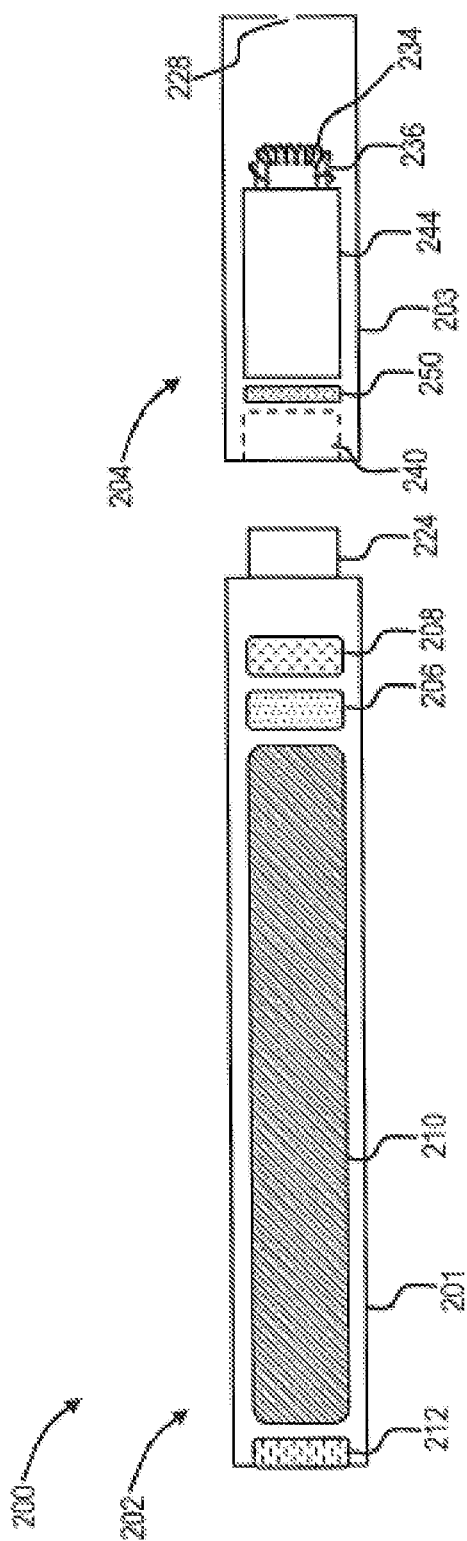
FIG. 10 is a sectional view through an electronic smoking article comprising a cartridge and a control body and including a reservoir housing according to an example embodiment of the present disclosure.

An exemplary embodiment of an electronic smoking article 200 is shown in FIG. 10. As illustrated therein, a control body 202 can be formed of a control body shell 201 that can include a control component 206, a flow sensor 208, a battery 210, and an LED 212. A cartridge 204 can be formed of a cartridge shell 203 enclosing a reservoir housing 244 that is in fluid communication with a liquid transport element 236 adapted to wick or otherwise transport an aerosol precursor composition stored in the reservoir housing to a heater 234. An opening 228 may be present in the cartridge shell 203 to allow for egress of formed aerosol from the cartridge 204. Such components are representative of the components that may be present in a cartridge and are not intended to limit the scope of cartridge components that are encompassed by the present disclosure. The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. The cartridge 204 also may include one or more electronic components 250, which may include an IC, a memory component, a sensor, or the like. The electronic component 250 may be adapted to communicate with the control component 206. The various components of an electronic smoking device according to the present disclosure can be chosen from components described in the art and commercially available.

In various embodiments, the aerosol precursor composition can comprise a flavorant comprising at least one tobacco-derived pyrazine. Exemplary formulations for aerosol precursor materials that may be used according to the present disclosure are described in U.S. Pat. No. 7,217,320 to Robinson et al.; U.S. Pat. Pub. Nos. 2013/0008457 to Zheng et al.; 2013/0213417 to Chong et al.; 2014/0060554 to Collett et al.; and 2014/0000638 to Sebastian et al., the disclosures of which are incorporated herein by reference in their entirety.

Other aerosol precursors that can incorporate the tobacco-derived pyrazines described herein include the aerosol precursors that have been incorporated in the VUSE® product by R.J. REYNOLDS® Vapor Company, the BLU™ product by IMPERIAL TOBACCO®, the MISTIC MENTHOL® product by MISTIC® Ecigs, and the VYPE® product by CN CREATIVE® Ltd. Also desirable are the so-called "smoke juices" for electronic cigarettes that have been available from JOHNSON CREEK ENTERPRISES® LLC.

EXPERIMENTAL

Aspects of the present invention are more fully illustrated by the following examples, which are set forth to illustrate certain aspects of the present invention and are not to be construed as limiting thereof.

Example 1

Glucose is produced from raw tobacco materials. Three sets of delignifications and saccharifications are performed. Each set consists of grinding (mechanically pulping) tobacco stalk biomass for two delignifications in a large delignification draft tube tank with a rough working volume of about 60 gallons. 14 kilograms (dry weight) of tobacco stalk is used in each delignification. After grinding the tobacco stalk biomass, 10 kg of delignified pulp remains for each delignification.

The delignified pulp is then rinsed, dewatered, and rinsed again. The pH is adjusted to 4.8, and then the pulp is dewatered again to obtain a pulp ready for enzymatic saccharification. A two addition saccharification is performed, starting with 5% solids and a 5% enzyme loading level on a dry weight basis. After this runs for 24 hours, a second addition of pulp is added to the mash and run for an additional 24 hours.

The residual solids are removed from the mash and the liquids are moved to the evaporator to condense. The resultant concentrated glucose syrup has a sugar makeup of 84.4% by weight glucose and 15.6% xylose by weight.

Example 2

At least one sugar material is produced from raw tobacco materials. Raw tobacco material (e.g., flue cured stalk, green stalk residual biomass, green plant residual biomass, dried stalk residual biomass, burley stalk that has been harvested within 4 weeks after the final leaf removal, burley root, etc.) is dried, washed and chipped. The first step is to isolate the cellulose from the biomass material and then in a second step, to convert the cellulose to sugar.

Three tobacco fractionations are carried out in a pilot scale batch reactor with temperature and pressure control. The raw materials are first screened using a 4 mm screen so that the small particles that could potentially block the flow of solvent within the biomass can be removed. The selected raw materials are treated in aqueous butanol with a solid to solvent weight ratio of about 1:5 to about 1:10 (water:butanol=1:1). The mixture is heated at 178° C. for 30-60 min under stirring, and in the presence of enough sulfuric acid to drop pH to about 2. Successful fractionation is achieved in all three cases.

5 Kg dry raw material is used. The process starts with 1:5 solid to solvent ratio. The flow does not develop inside the reactor, therefore, additional solvent is added to increase the solid to solvent ratio to about 1:7. The process is performed at 100 PSI initial pressure for 60 minutes at temperature of 178° C. After complete wash, about 37.19% pulp is recovered, about 30.53% lignin out, and Kapa number is 76.

6 Kg dry raw material is used. The process is started with a 1:7 solid to solvent ratio, but again due to lack of solvent flow within the reactor, additional solvent is added to increase the solid to solvent ratio to about 1:10. Because some time is lost without any flow, the process time is increased to 120 minutes and as a result, the fiber is mostly burned out. The process is performed with 100 PSI initial pressure and temperature of 178° C. After complete wash, about 43.5% is recovered pulp, about 16.95% lignin out, and Kapa number is 82.8.

7.54 Kg dry raw material is used. The process is started with a 1:10 solid to solvent ratio and solvent flow is good. The process is performed at 100 PSI initial pressure for 60 minutes at temperature of 178° C. After complete wash, about 37.32% pulp is recovered, about 30.6% lignin out, and Kapa number is 81.6.

Following fractionation, the cellulose pulp (i.e., the solids) is separated from the residual liquid. After processing several biomasses from tobacco, the average pulp yield is 42%, of which 39% is converted to sugar via enzymatic hydrolysis, yielding on average 18% sugar from dry biomass. 5% loading and CTEC-2 enzymes are used for the enzymatic hydrolysis of the pulp. The green leaf/stalk biomass yielded the highest amount of sugar and the pre-extracted cured flue cured stalk yielded the least amount of sugar. Chemical analyses of these sugars is completed and specific sugar analyses confirm that the sugar is glucose. Very low levels of fructose and sucrose are reported, however, the sugar for all intents and purposes is glucose.

The resultant sugar is then evaporated to increase the concentration to about 70% or greater. To avoid any potential secondary reaction or destruction of the sugar, a heated jacket and vacuum are used to increase sugar density instead of a boiling process.

Example 3

A glucose syrup having a reduced xylose concentration is produced from raw tobacco materials. The process described in Example 1 or 2 above is followed to produce a glucose syrup. However, in order to eliminate the xylose from the syrup, xylanases are used to remove the hemicellulose before the final saccharification. Three different types of xylanase enzymes are used (Rhyzyme®, Pulpzyme® HC & HC 2500, Dyadic® Xylanase, and combinations thereof).

Pulpzyme® HC & HC 2500 is the only enzyme that released xylose and no glucose. However, the release of xylose was lower than desired. Adding another xylanase enzyme showed good hydrolysis of the hemicellulose but also equal hydrolysis of cellulose. However, a combination of xylanases enabled removal of half of the still available hemicellulose in this step, which lowered the xylose in the glucose syrup by about 50%, but did not eliminate it.

Example 4

High fructose tobacco syrup is produced using commercial immobilized glucose isomerase (also referred to as Sweetzyme type IT®) and a tobacco glucose syrup made as set forth in Example 1 or 2. The experiment is conducted at 55° C. and an initial tobacco glucose concentration of 13%. The enzyme (45 g) is hydrated prior to adding it to 4 L of Tris-buffer media (pH 7.5) containing the glucose. Fructose production is approximately 0.5 g/g. Final glucose and fructose concentrations are 275 g/L and 225 g/L, respectively.

Example 5

Tobacco materials undergo acidic clarification and precipitation to obtain RuBisCO (F1 protein).

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.6. This protein-containing extract is clarified first by passing the extract through a decanter. The pH of the protein-containing extract is adjusted to 5.9 using hydrochloric acid. Diatomaceous earth is optionally added to the extract, the mixture is stirred for 15 minutes, and then passed through a filter press.

The resulting clarified, protein-containing extract is treated with citric acid and hydrochloric acid to adjust the pH to 4.92. The pH-adjusted extract is left to sit for 47 hours. Liquid is decanted from the top of the mixture and a settled solid at the bottom of the mixture is obtained and processed on a 1.4 μm ceramic filter using tangential flow filtration. The retentate therefrom is concentrated to give a protein-enriched tobacco-derived material. The materials thus obtained comprise between about 85 and about 99% protein by weight.

Example 6

Tobacco materials undergo acidic clarification and precipitation to obtain RuBisCO (F1 protein) and F2 protein fractions.

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter. The pH of the protein-containing extract is adjusted to 5.9 using hydrochloric acid. Diatomaceous earth is optionally added to the extract, the mixture is stirred for 15 minutes, and then passed through a filter press. The filtrate is washed with water, pH adjusted to 5.9 to increase recovery of protein.

The resulting clarified, protein-containing extract is processed on a 500 kDa reverse osmosis filter using tangential flow filtration. The retentate is washed with a glycine solution (75 mM glycine at pH 10.5) to give a RuBisCO-enriched tobacco-derived material retentate (comprising about 75-85% protein by weight). The permeate is cooled to 8° C. and processed on a 1 kDa reverse osmosis filter using tangential flow filtration. The 1 kDa retentate is washed with the glycine solution and concentrated to give a F2 protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 7

Tobacco materials undergo acidic clarification and precipitation to obtain RuBisCO (F1 protein) and F2 protein fractions.

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.7. This protein-containing extract is clarified first by passing the extract through a decanter. The pH of the protein-containing extract is adjusted to 5.9 using hydrochloric acid. Diatomaceous earth is added to the extract, the mixture is stirred for 15 minutes, and then passed through a filter press.

The resulting clarified, protein-containing extract is treated with hydrochloric acid to adjust the pH to 4.98. The pH-adjusted extract is left to sit for 60 hours. Liquid is decanted from the top of the mixture and a settled solid at the bottom of the mixture is obtained and processed on a 1.4 μm ceramic filter using tangential flow filtration. The retentate therefrom is concentrated to give a protein-enriched tobacco-derived material. The materials thus obtained comprise between about 85 and about 99% protein by weight.

Example 8

Tobacco materials undergo basic clarification to obtain RuBisCO (F1 protein) and F2 protein.

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.5. This protein-containing extract is clarified first by passing the extract through a decanter. The pH of the protein-containing extract is adjusted to 10.5 using sodium hydroxide. Activated carbon is added and diatomaceous earth is added to the extract, the mixture is stirred for 15 minutes, and then brought into contact with a filter press. As the mixture was not passing through the filter press, the pH of the mixture is adjusted to 5.9 using hydrochloric acid and then passes through the filter press.

The resulting clarified, protein-containing permeate is processed on a 500 kDa reverse osmosis filter using tangential flow filtration. The retentate is washed with a glycine solution (75 mM glycine at pH 10.5), giving a RuBisCO protein-containing retentate (comprising about 75-85% protein by weight) and stored. The permeate is cooled to 8° C. and processed on a 1 kDa reverse osmosis filter using tangential flow filtration. The retentate is washed with the glycine solution and concentrated to give a F2 fraction protein-enriched tobacco-derived material comprising about 30-40% F2 protein by weight.

Example 9

Tobacco materials undergo acidic clarification and precipitation to obtain RuBisCO (F1 protein) and F2 protein fractions.

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter. The pH of the protein-containing extract is adjusted to 5.9 using hydrochloric acid. Activated carbon is added and diatomaceous earth is added to the extract, the mixture is stirred for 15 minutes, and then passed through a filter press. The resulting clarified, protein-containing permeate is processed on a 500 kDa reverse osmosis filter using tangential flow filtration. The retentate is washed with a glycine solution (75 mM glycine at pH 10.5), giving RuBisCO protein-containing retentate (comprising about 75-85% protein by weight), which is stored. The permeate is cooled to 8° C. and processed on a 1 kDa reverse osmosis filter using tangential flow filtration. The retentate is washed with the glycine solution and concentrated to give a F2 fraction protein-enriched tobacco-derived material comprising about 30-40% F2 protein by weight.

Example 10

Tobacco materials undergo acidic clarification and precipitation to obtain RuBisCO (F1 protein) and F2 protein fractions. The combined RuBisCO and F2 proteins are isolated and subsequently separated.

Tobacco plants are harvested, chipped, and homogenized in a disintegrator by adding water thereto and the material is then passed into a horizontal screw press for liquid extraction. The liquid protein-containing extract thus obtained is a green juice having a pH of 5.6. The pH of the protein-containing extract is adjusted to 7.10 using sodium hydroxide. Diatomaceous earth is added to the extract, the mixture is stirred for 15 minutes, and then passed through a filter press. The resulting clarified, protein-containing permeate is processed on a 1 kDa filter using tangential flow filtration. The retentate comprises a mixture of RuBisCO and F2 proteins and comprises approximately 50% protein.

Example 11

Samples of F1 and F2 protein derived from tobacco materials are subjected to acid hydrolysis or enzymatic hydrolysis. F1 protein predominantly comprises ribulose-1, 5-bisphosphate carboxylase oxygenase (commonly referred to as RuBisCO), whose subunit molecular weight is about 550 kD. F2 protein generally contains a mixture of proteins and peptides with molecular weights ranging from about 3 kD to about 100 kD and may also contain other compounds including sugars, vitamins, alkaloids, flavors, and amino acids.

Representative samples of both F1 and F2 proteins are tested for the initial level of free amino acids present before hydrolysis and the level of amino acids formed after acid hydrolysis. See, Table 1 below. Based on the results, F1 has a higher level of protein available for hydrolysis.

TABLE 1

Amino Acids Before and After Acid Hydrolysis

| Protein | Free Amino Acids Before Hydrolysis | Total Amino Acids After Acid Hydrolysis |
| --- | --- | --- |
| F1 | 3.18% | 47.9% |
| F2 | 5.66% | 26.6% |

F1 and F2 tobacco-derived protein samples are subjected to enzymatic hydrolysis using Maxazyme® NNP DS, Accelerzyme® CPG, and Validase® FP Concentrate enzymes. One gram of tobacco-derived protein is weighed into a 125 mL Erlenmeyer flask. The enzymes are them weighed out into the same flask. The samples are diluted with 100 mL of deionized water. The pH is adjusted using either dilute hydrochloric acid or dilute sodium hydroxide depending on the pH of the mixture and the pH required for the enzymes. For Maxazyme® NNP DS and Validase® FP Concentrate, the pH is adjusted to about 7. For Accelerzyme® CPG, the pH is adjusted to about 5. For mixtures of Maxazyme® NNP DS and Accelerzyme® CPG, the pH is adjusted to about 6, midway between the optimal pH for each. The flasks are placed in a water bath at 50° C. for the duration of the hydrolysis followed by 10 minutes at 85° C. to deactivate the enzymes. The enzymatically hydrolyzed samples are filtered through Whatman 0.45µ PVDF autovials and analyzed directed by SEC and total amino acids analysis.

F1 is initially hydrolyzed using various combinations of Maxazyme® NNP DS, Accelerzyme® CPG, and Validase® FP Concentrate enzymes. The percentage of amino acids after hydrolysis are shown in Table 2 below.

TABLE 2

F1 Enzymatic Hydrolysis Conditions

| Maxazyme ® NNP DS (mg) | Validase ® FP Concentrate (mg) | Accelerzyme ® CPG (mg) | Time (h) | % Amino Acids |
| --- | --- | --- | --- | --- |
| 50 | 0 | 0 | 4 | 10.59 |
| 50 | 0 | 0 | 20 | 15.34 |
| 50 | 0 | 50 | 20 | 17.81 |
| 50 | 50 | 0 | 20 | 38.6 |
| 50 | 50 | 0 | 20 | 38.7 |
| 50 | 50 | 0 | 20 | 39 |
| 100 | 100 | 0 | 20 | 42.4 |
| 25 | 25 | 0 | 20 | 34.5 |
| 25 | 25 | 0 | 4 | 20.3 |
| 25 | 100 | 0 | 4 | 29.5 |
| 100 | 100 | 0 | 4 | 33.1 |
| 100 | 25 | 0 | 4 | 21.7 |
| 100 | 25 | 0 | 20 | 34.3 |
| 25 | 100 | 0 | 20 | 39.6 |

A variety of conditions are tested on F2 protein. No major increase in amino acids over the level already present before hydrolysis is observed. Since the F2 sample is only about 27% protein, the remaining constituents such as fiber and ash could be interfering with the enzymes.

TABLE 3

| | F2 Enzymatic Hydrolysis Conditions | | | |
| --- | --- | --- | --- | --- |
| Maxazyme ® NNP DS (mg) | Validase ® FP Concentrate (mg) | Accelerzyme ® CPG (mg) | Time (h) | % Amino Acids |
| 50 | 50 | 0 | 20 | 6.98 |
| 50 | 0 | 50 | 20 | 4.21 |
| 100 | 0 | 0 | 20 | 4.13 |
| 0 | 100 | 0 | 20 | 8.84 |
| 0 | 0 | 100 | 20 | 4.32 |

From the data and models derived from the data, it is determined that the amount of Maxazyme® NNP DS is not relevant and longer times and higher amounts of Validase® FP Concentrate increases the amount of amino acids released during hydrolysis, although large increases in the amount of Validase® FP Concentrate results in only a small increase in the amount of amino acids released. In a preferred embodiment, the optimal hydrolysis conditions are F1 protein and about 200 mg Validase® FP Concentrate for about 20 hours, which results in a release of 44.1% amino acids.

This experiment illustrates that enzymatic hydrolysis can successfully breakdown tobacco-derived protein into amino acids.

Example 12

Potassium nitrate crystals are produced from tobacco raw materials.

Burley stems (1400 lbs.) are extracted with water (14000 lbs.). This is accomplished in two 700 lb. batches due to extraction-tank volume limitations. The first batch of stems is allowed to extract overnight at 160° and the second 700 lb. batch is extracted for 2 hours at 160° F. The aqueous fraction is separated from the fibrous tobacco residue by centrifugation. The aqueous fraction is then concentrated under vacuum to a total solids content of approximately 45%. The concentrated extract (approx. 500 lbs.) is transferred to 5 gallon buckets and placed in a freezer at 32° F. overnight.

After approximately 36 hours at 32° F., the concentrated extract is transferred to a centrifuge containing a <10 μm filter bag. Centrifugation removes most of the non-potassium nitrate crystal material leaving behind 55 lbs. of "dirty" potassium nitrate. 50 lbs. of the dirty crystals (separated into 5 10 lb. batches) are mixed on a 1 to 1 basis with water and heated until completely dissolved. The dissolved crystal solutions are poured through 10 μm filter bags as they are transferred to 5 gallon buckets. The buckets are allowed to slowly cool to room temperature before being placed in a 35° F. cooler overnight. After 24 hours in the cooler, each of the 5 gallon buckets of extract is decanted through a >500 μm filter bag. The filter bag is used to separate the extract from the $KNO_3$ crystals that formed in the bottom of the buckets. A total of 29.5 lbs. of moderately clean $KNO_3$ crystals are thus obtained.

Example 13

Potassium nitrate crystals are produced from tobacco raw materials.

An extraction process as described in Example 12 is performed (1400 lbs. of burley stems extracted in a 10:1 ratio with 14000 lbs. of water). However, multiple filtration steps are used to produce a cleaner concentrated extract.

First, the aqueous fraction is filtered through a 10 μm filter and passed through a centrifuge with a <10 μm filter bag in place. The aqueous fraction is then concentrated under vacuum to a total solids content of approximately 20%, after which it is passed back through a 10 μm sock filter and a cleaned <10 μm centrifuge filter for further removal of suspended solids. The extract is then pumped back to the evaporator and concentrated to a final solids content of approximately 38%.

The concentrated extract (379 lbs.) is then transferred to 5 gallon buckets and allowed to cool to room temperature overnight before being placed in a 35° F. chiller for 24 hours. After the 24 hours has passed, each of the 5 gallon buckets of extract is decanted into a new five gallon bucket while passing through a >500 μm filter bag. The filter bag is used to separate the extract from the $KNO_3$ crystals that have formed in the bottom of the buckets. Included in, and trapped with the $KNO_3$ crystals is a significant amount of tobacco solids. In total, 80.0 lbs. of $KNO_3$ crystals and tobacco solids are removed during this initial crystallization. To ensure maximum yields are obtained, the decanted extract is placed back in the 35° F. cooler for a further 24 hours and the decanting/filtering process is repeated. This results in a further 22.5 lbs. of $KNO_3$ crystals and tobacco solids being obtained. The remaining extract is then placed in a 28° F. freezer for 24 hours. Repeating the decanting/filtering steps results in the further collection of 23.0 lbs. of $KNO_3$ crystals and tobacco solids. The remaining extract is again placed in the freezer for another 24 hours, but no further crystallization is noted. The total yield of $KNO_3$ crystals and tobacco solids from the original 379 lbs. of concentrated extract is 125.5 lbs.

The inclusion rate of other tobacco extractives in the first generation of potassium nitrate crystals produced is deemed to be excessive, necessitating further refinement. This is accomplished by dissolving equal aliquots of the first generation crystals with tap water and heating until dissolved. Upon complete dissolution, the liquid is decanted through a 5 μm sock filter, placed in the 35° F. cooler overnight and allowed to regenerate crystals. The resulting Generation 2 crystals are much cleaner, but still not of a high enough purity to meet the expected requirements of future work. In order to ensure adequate purity, the Generation 2 crystals are subjected to the refining process once again. After drying using an equilibration table, the resulting crystals have a combined mass of 41.0 lbs. and are deemed to be of high enough purity.

The percent of nitrate in the crystals generated at each of the crystal-generating steps ranges from about 58.5% to about 61.5%. The molecular weight of potassium nitrate ($KNO_3$) is 101.1 amu. Of this, 61.1% is nitrate ion ($NO_3^-$). Accordingly, even the 'dirty' crystals (prior to any refinement) are almost pure potassium nitrate. The further refinement of the potassium nitrate crystals leads to incremental increases in purity with the twice-washed and regenerated crystals being almost pure potassium nitrate.

The 1400 lbs. of infeed burley stem has a nitrate concentration of 10.3% per analysis by LANCASTER LABORATORIES®. The maximum yield of the extraction is 144.2 lbs. (1400 lbs. of stem*10.3% ($NO_3$)$^-$) of nitrate. Based on the amount of concentrated extract that is obtained (379 lbs.) and the nitrate concentration of the concentrated extract (12.18%), there could have been at most 46.2 lbs. of nitrate recovered from the infeed stems. 32% of the possible nitrate is recovered. Thus, 68% of the nitrate in the infeed stems is not extracted and thus never available for concentration and crystal generation.

As previously stated, the 379 lbs. of concentrated extract had a nitrate concentration of 12.2%. Thus, 46.2 lbs. of nitrate crystals could be recovered if 100% recovery was obtained. However, only 18.6 lbs. of nitrate crystals were recovered. This indicates a loss of 59.7% of the extracted nitrate. This loss of nitrate can be much smaller if the liquor from the crystal generations is collected, concentrated and allowed to recrystallize.

The infeed burley stem contains on average almost 11% (10.98%) nitrate and is moderately consistent for throughout each trial. The concentration of nitrate in the extraction tanks is consistently in the 0.48% to 0.78% range. The overnight extraction appears to have minimal effect on the amount of nitrate extracted from the burley stems as the percentage extracted (0.64%) is within the range of the 2 hour extractions. The nitrate concentration of the final concentrated extract is 12.3% for a first trial and a similar 12.2% for a second trial.

Example 14

Two types of cells are used to investigate the electrode performance of ammonia production by electrochemically reducing nitrate.

A glass cell with electrode geometric area at 4.2cm$^2$ is initially used for material screening. Two glass cell compartments separated by a single piece of Nafion 115 serve as reservoirs for catholyte (1M potassium nitrate (SIGMA-ALDRICH®)) and anolyte (1M potassium hydroxide (reagent grade)), respectively. Platinum foil, which facilitates oxygen evolution reaction in aqueous solution, is used as the anode material. The materials adopted as cathode are nickel, copper and graphite sheet. In the cathode compartment, pH is monitored and the solution is stirred continuously to ensure solution homogeneity. The resulting gas at cathode carried by argon is directed to the scrubber (0.1M sulfuric acid) and sampled periodically at the scrubber outlet for gas chromatography (GC) analysis. While maintaining the system closed, the catholyte and scrubber solution are sampled at 30 min interval during the course of testing for ion chromatography (IC) analysis. The current is controlled by a laboratory DC power supply.

Sampled solutions are diluted properly for ion chromatography (DIONEX® equipment) analysis quantifying the concentration of nitrate, nitrite and ammonium ions. Resulting gas sampled at 100 µL is analyzed by the gas chromatography (HEWLETT-PACKARD® equipment) for quantifying the volume ratio of nitrogen, hydrogen and oxygen.

The performance of nickel, copper and graphite as cathode materials for ammonia production through nitrate reduction is examined. These candidates are initially evaluated in the glass cell. Among the selected materials, nickel possesses the highest ammonium yield and consumes the least amount nitrate. On the other hand, copper reduces the highest quantity of nitrate, however, the majority of the nitrate is reduced to form nitrite rather than ammonium. In the case of graphite, the ammonium yield is the lowest among the three materials. For passing the same amount of charge, copper shows the highest efficiency reducing nitrate to nitrite (2e) and ammonium (8e) with minimal gas evolution.

The impact of electrolyte composition on ammonium formation is also investigated in the glass cell configuration. Since the ammonia is more likely to be liberated from the electrolyte at high pH in theory, it is expected that the resulting ammonia would present as gas phase and be mostly trapped in the acid scrubber. However, based on the IC analysis, the majority of ammonium ions are found residing in the high pH catholyte. In the case of copper, the results indicates that the rate ammonia production is low in the beginning, but increases more drastically in the latter half of the test, implying that the nitrite content and the solution pH can influence the rate of ammonium formation. To assess this point, the cell tests are re-run at identical conditions for 2.5 hour. Instead of pure nitrate solution, catholyte with equal amount (0.5M) of nitrate, nitrite and KOH is adopted. The results show increased ammonia quantity for graphite and copper electrodes. The graphite electrode, in this case, shows comparable ammonium yield to that of nickel. Furthermore, nickel and copper electrodes show a poor nitrogen mass balance, indicating that varying the catholyte composition could also promote the nitrogen to react via other pathway(s) (e.g., forming $N_2$) and/or $N_2$). However, the poor diffusion mechanism in the glass cell could magnify the composition dependency on electrode performance. Therefore, the MP cell is used to further evaluate this point.

An MP cell (ELECTROCELL®, Denmark) is constructed to evaluate the performance of various electrodes. Similar to the glass cell, a platinum metal sheet is adopted as the anode material. Nickel, copper and graphite felt are evaluated as cathode materials. Two cell compartments equipped with turbulent promoter are separated by a single piece of Nafion 115 allowing individual electrolyte circulation. 1M $KNO_3$ is adopted as initial catholyte and concentrate KOH is used as anolyte. The electrolytes are circulating at the flow rate ranging from 800 ml/min to1500 ml/min. In addition, sulfuric acid scrubber is incorporated to trap the resulting ammonia gas produced from the cathode. The current density of the cell is maintained at 100 mA/cm$^2$ or 200 mA/cm$^2$ throughout the test (corresponding to total 10 A or 20 A for a 100 cm$^2$ cell). The catholyte and scrubber solutions are sampled periodically for IC analysis. The resulting gas carried by argon is also sampled every 30 min at the scrubber outlet for GC analysis. In particular, the argon flow rate is calibrated before each test allowing quantitative gas analysis. The Arbin test equipment controlled the current of the electrochemical process.

The performance of the nickel and copper electrode is examined in the MP cell. In this test, 1M $KNO_3$ and 4M KOH at 1000 ml are used as initial catholyte and anolyte, respectively, and the current density is controlled at 100 mA/cm$^2$. The quantity of nitrate destruction is similar for both materials during the course of the experiment. However, the resulting nitrite content is significantly higher for copper electrode as compared to that for nickel. On the contrary, the quantity of ammonium yield on the nickel cell is ~50% higher than that for copper. This result is consistent with the observation in glass cell and again suggests that nickel converts nitrate to ammonium more effectively as compared to copper.

The selected materials are again tested in the MP cell where the current density is increased to 200 mA/cm$^2$ with reasonable applied voltage. Nickel and copper showed similar characteristics to those observed in the glass cell. When running the experiment to the point where the nitrate content is low (or ammonium content is high), the nickel electrode seems to produce more nitrite rather than ammonium under this condition, suggesting the mass transport could be the limiting factor. Thereafter, a porous electrode is adopted to assess this point and more effective nitrate reduction is observed. In addition, the ammonium formation rate seems to not be strongly affected even when the nitrate content is low in the porous electrode cell. The associated gas evolution is also decreased as using a porous electrode.

Up to this point, all the tests are performed using KOH solution as the anolyte. However, since the KOH is consumed during the electrolysis and may not be readily available, another set of experiments is conducted using sulfuric acid as the anolyte. In this case, it is the proton that passes through the ion exchange membrane instead of the potassium ion and the source of proton is water, which is not difficult to obtain. The testing conditions are kept the same as described above, except 1M $H_2SO_4$ is used as the anolyte. The copper-plated felt produces higher overall nitrite content than that for untreated graphite felt. However, the nitrite content for the copper-plated felt in this case is not as high as that using KOH as anolyte. It could be possible that the copper deposited on the felt is attacked by the acid during initial circulation (usually took 30 min to equilibrate before the test). The ammonium yield are lower for both materials than in previous tests. In the case of untreated graphite felt, the nitrite content is significantly higher than in previous tests, leading to ammonium formed at lower quantity.

Overall, producing ammonia via nitrate reduction in an electrochemical flow cell is promising. The use of either KOH or $H_2SO_4$ as anolyte is feasible and the anolyte management in larger scale has been suggested. The estimated coulombic efficiency for this purpose is between 30%-50% for the porous electrode cell.

Example 15

Electrochemical reduction of potassium nitrate derived from raw tobacco materials is used to produce tobacco-derived ammonium hydroxide. The effect of impurities present in the potassium nitrate derived from raw tobacco materials is evaluated.

An MP cell (ElectroCell, Denmark) is constructed to evaluate the performance of high surface area electrodes. In the MP cell, a Pt/Nb clad metal sheet is adopted as the anode material and a felt electrode is used as the cathode. The anolyte compartment is equipped with turbulence promoters and is separated from the cathode side by a single piece of Nafion 115 allowing individual electrolyte circulation. During operation, concentrated KOH is used as anolyte. The current density of the cell is maintained at 200 $mA/cm^2$ throughout the test (corresponding to total 20 A for a 100 $cm^2$ cell). The cathode compartment in this case comprises a graphite current carrier and a graphite felt cathode (total thickness of 15 mm compressed to 12 mm). The felt completely fills the catholyte compartment (no turbulence promoter), forcing the electrolyte to flow through the felt perpendicular to the current flow.

Subsequently, the cell is modified to achieve 200 $cm^2$ geometric cell area (a regular MP cell has 100 $cm^2$ geometric area) and accommodate total current of 40 A. The cell is constructed in a way that two cathodes reside on each side of the anode (two nickel metal sheet wielded together) and, in this case, both sides of the anode are used to conduct the current.

An additional scrubber (deionized water) is incorporated between the catholyte reservoir and the acid scrubber to trap the ammonia gas and generate ammonium hydroxide solution. The catholyte and scrubber solutions are sampled periodically for IC analysis. The resulting gas carried by argon is also sampled every 30 min at the scrubber outlet for GC analysis. In particular, the argon flow rate is calibrated before each test allowing quantitative gas analysis. The current of the electrochemical process is controlled by the Arbin test equipment.

Electroplating copper is performed in the test cell prior to nitrate reducing operation. In the process of electroplating, anolyte (0.5M sulfuric acid) and catholyte (0.1M copper sulfate) are circulated to each compartment while current of 5 $mA/cm^2$ is applied for 30 min. After plating, each compartment is rinsed with deionized water while maintaining polarization of the electrodes to retain the copper in the graphite felt.

Sampled solutions are diluted appropriately for ion chromatography (DIONEX®) analysis quantifying the concentration of nitrate, nitrite and ammonium ions. Resulting gas sampled at 100 µL is analyzed by the gas chromatography (GOW MAC® and HEWLETT-PACKARD®) for quantifying the volume ratio of hydrogen (GOW MAC®) and nitrous oxide (HP). In particular, a PLOT-Q column (QUADREX®) is incorporated in HP for nitrous oxide analysis.

Graphite felt cathode is successfully adopted for the reduction of nitrate and the electrolysis time is extended to consume the nitrate/nitrite species completely. The initial electrolyses are accompanied by significant hydrogen evolution and showed only a 45% coulombic efficiency for ammonium production. To improve the efficiency, copper is electrochemically deposited onto the graphite felt. With 3 $mg/cm^2$ copper loading on the graphite felt cathode, hydrogen formation is significantly reduced and the coulombic efficiency for ammonium production reached 68%.

Since ammonium hydroxide at high concentration is desirable as product, the ammonia production rate is further increased by raising the current. By modifying the MP cell, the operating current is increased by a factor of 2 and the ammonium hydroxide concentration is raised by 1.7×. The modified MP cell with copper-coated felt cathodes is then used to produce ammonium hydroxide solution with $KNO_3$ derived from tobacco materials.

Three different grades (1×, 2× and 3×) of tobacco-derived potassium nitrate, representing 1 to 3 re-crystallizations, are electrochemically reduced. The 3× sample has the highest purity of the three whereas the 1× sample appears to contain significant insoluble impurities. The 1× and 2× solutions were filtered with 0.6 µm filter paper before use, whereas the 3× sample was used as received.

In the initial experiments with the 3× and 1× materials, the cell is operated at a constant catholyte inlet pressure of approximately 3 psi, and as a result, there is some variation in flow rate (as described below, subsequent experiments are performed at a constant flow rate). The results are compared with those obtained from reagent grade $KNO_3$ under the same operating conditions. In general, the tobacco-derived $KNO_3$ appears to generate more hydrogen compared to the reagent grade $KNO_3$. The 1× nitrate shows the highest hydrogen formation and reagent grade has the lowest. Since the catholyte inlet pressure is controlled in this data set, it is suspected that the flow rate for the 1× containing catholyte is insufficient due to possible blockage in the felt by insoluble impurities, which would likely raise the rate of hydrogen formation. As a result, the coulombic efficiency of ammonium production for 1× is relatively low (59%) due to the high hydrogen production. The peak coulombic efficiency for the case of 3× material reached 70%, which is similar to that of the reagent grade nitrate.

To assess the influence of flow rate, a second set of experiments is conducted maintaining catholyte flow rate above 2000 ml/min (higher than in previous tests which were in the range <1000 ml/min). In this set of testing, the tobacco-derived 3× and 2× potassium nitrate materials are used. The data of 3× material obtained at constant pressure is also compared. The coulombic efficiency for ammonia production reaches as high as 86% at the higher flow rate, demonstrating a significant influence. The observation for improved efficiency is attributed to the enhanced mass transport of the nitrate/nitrite species in the electrode at higher flow rate. The quantity of hydrogen evolution is also reduced with the higher ammonium production efficiency. However, the higher ammonium efficiency does not necessarily lead to higher ammonium concentration in the water scrubber. Without being limited by theory, it is believed that the extra ammonium gained with higher efficiency is likely to reside in the catholyte rather than in the water scrubber.

Since ammonium hydroxide (water scrubber) is the desirable product for subsequent synthesis, factors controlling the ammonium distribution between the catholyte and gas phase are investigated. It is discovered that increasing the pH of catholyte has a remarkable impact on ammonium distribution. The results indicate that the majority of the ammonium generated can be transferred to the scrubber using catholyte prepared at high KOH concentration. It is possible that increasing the temperature and further gas sparging might also facilitate the ammonia transfer toward scrubber. More importantly, the resulting catholyte, in this case, with low nitrate, nitrite and ammonium levels, can possibly be reused as anolyte in subsequent batches, thus recycling the KOH.

A test is also performed where nitrate is added during the electrolysis. The results in terms of ammonium production are consistent with the ones using equal amount of total nitrate initially. Considering a continuous type operation, adding nitrate during the process is feasible. In addition, as indicated by GC analysis, the resulting gas contains negligible amount of nitrous oxide. This present work produces approximately 1.5 L of 2.7M of tobacco-derived ammonium hydroxide.

Example 16

Two different types of protein and three different hydrolysis conditions are used to make amino acids that are then tested for their suitability in making tobacco-derived pyrazines. The two types of protein used are referred to as F1 and F2, as defined in Example 11 above.

For acid hydrolysis, protein derived from tobacco materials is subjected to acid hydrolysis to make amino acids. 1 gram of the tobacco-derived protein in 100 mL of 6 N hydrochloric acid (HCL) is heated to 180° C. in a MARSX® microwave system with a 15 minute ramp and a 15 minute hold.

For enzyme hydrolysis, 1 gram of protein in 100 mL of water is combined with the enzyme(s). The pH is adjusted to 7 and the mixture is heated to 50° C. for 20 hours in a water bath. The enzymes are then deactivated by heating the mixture at 85° C. for 10 minutes.

The control experiment uses no amino acids.

In each of the three experiments, 1 mL of high fructose tobacco syrup (HFTS) containing 23.10% glucose and 21.9% fructose is used as the sugar source. 1 mL of ammonium hydroxide ($NH_4OH$) solution containing 28.0-30.0 ammonia ($NH_3$) is used as the additive. The HFTS and $NH_4OH$ solution are added directly to the hydrolyzed protein mixture, and the pH is adjusted with dilute sodium hydroxide (NaOH) or dilute HCl as necessary. The mixture is heated to 140° C. using the MARSX® microwave system for 2 hours. The pH of the mixture becomes more acidic over the course of the reaction, so after the reaction is complete, the pH is again adjusted with NaOH as necessary to ensure that the pyrazines can be extracted into dichloromethane. The specifics of the reactants used in each experiment is set forth in Table 4 below.

TABLE 4

Types of Protein and Hydrolysis Conditions

| Sample Name | Protein Used | Hydrolysis Conditions |
|---|---|---|
| F1__None | F1 | None |
| F1__Acid | F1 | Acid |
| F1__50M/50V | F1 | Enzyme: 50M/50V* |
| F1__90V | F1 | Enzyme: 90V* |
| F2__None | F2 | None |
| F2__Acid | F2 | Acid |
| F2__50M/50V | F2 | Enzyme: 50M/50V* |
| F2__100V | F2 | Enzyme: 100V* |
| Control | n/a | n/a |

*#M = # mg Maxazyme ® NNP DS
V = # mg Validase ® FP Concentrate

Each of the dichloromethane extracts are analyzed by gas chromatography mass spectrometry (GC/MS) using the conditions set forth in Table 5 below.

TABLE 5

GC/MS Parameters

| | | |
|---|---|---|
| Column | Phase | DB-WAXETR |
| | Length | 30 m |
| | Internal Diameter | 0.250 mm |
| | Film Thickness | 0.25 μm |
| Oven Program | Initial Temperature | 30° C. |
| | Initial Time | 0.50 min |
| | Rate | 7.5° C./min |
| | Final Temperature | 260° C. |
| | Final Time | 12.83 min |
| MSD | Acquisition Mode | Scan |
| | Solvent Delay | 4 min |
| | Masses Scanned | 33-300 amu |
| | MS Source Temperature | 230° C. |
| | MS Quad Temperature | 150° C. |
| Injection | Temperature | 250° C. |
| | Volume | 1 μL |
| Column Flow | Flow Mode | Constant |
| | Flow Rate | 1 mL/min |
| | Purge Flow | 9.8 mL/min |
| | Purge Flow Time | 1.0 min |
| | Inlet Mode | Splitless |

The effects of the different types of protein and hydrolysis conditions are analyzed using the relative total area counts for the pyrazines formed, as illustrated in Table 6 below.

TABLE 6

Amino Acids and Pyrazines

| Name | Pyrazines Total Area | Amino Acids (mg) | Amino Acids after Pyrazines (mg) | Amino Acids Consumed (mg) | % Change in Amino Acids |
|---|---|---|---|---|---|
| F1__None | n/a | 31.8 | n/a | n/a | n/a |
| F1__Acid | 55.98 | 556 | 359 | 197 | 35% |
| F1__50M/50V | 73.03 | 382 | 234 | 148 | 39% |
| F1__90V | 83.87 | 389 | 247 | 142 | 37% |
| F2__None | 34.49 | 56.6 | n/a | n/a | n/a |
| F2__Acid | 47.62 | 207 | 143 | 64 | 31% |
| F2__50M/50V | 35.60 | 78 | 54 | 24 | 31% |
| F2__100V | 58.29 | 88.4 | n/a | n/a | n/a |
| Control | 30.68 | n/a | n/a | n/a | n/a |

Amino Acids from F1 are better at forming pyrazines than those from F2. For both F1 and F2, the best results are obtained using enzymatic hydrolysis, despite the fact that acid hydrolysis produced a higher percentage of amino acids. It is noted that the enzyme MAXAZYME® NNP DS is significantly cheaper than VALIDASE® FP Concentrate, which may account for the higher yields obtained with the latter.

The amount and distribution of amino acids formed for each type of protein under each set of hydrolysis conditions is also analyzed and illustrated in Table 6 above and in FIGS. 5a and 5b. F2 is dominated by glycine while F1 gives a broader distribution of amino acids.

The amount and distribution of amino acids is also analyzed after the pyrazines are formed so that the amount of amino acids consumed and percent change in amino acids can be calculated. See, Table 6 above and FIGS. 6a, 6b, 7a and 7b. A larger amount of amino acids is consumed when a larger amount is available, but in all cases about a third of the available amino acids is consumed. Different amino acids are favored depending on the type of protein and hydrolysis conditions used.

In conclusion, tobacco-derived pyrazines can be made from HFTS and amino acids obtained from the enzymatic hydrolysis of F1 protein. F2 protein is another potential source of tobacco-derived amino acids. Additionally, the protein can be hydrolyzed by acid hydrolysis instead of enzymatic hydrolysis. F1 protein performs better than F2 protein, but they produce qualitatively similar results. A larger amount of amino acids is consumed when a larger amount was available, but in all cases about a third of the available amino acids is consumed.

Example 17

Tobacco-derived pyrazines are produced according to Example 16 above using high fructose tobacco syrup (HFTS) as the carbon source and amino acids from the enzymatic hydrolysis of F1 Rubisco protein as the nitrogen source. The pyrazine product is purified and fractionated using distillation.

A method is developed using the WATERS AQUITY® UPCL H-Class system with UV detection for the relative quantitation and identification of the tobacco-derived pyrazines. A GC/MS profile of the pyrazine fractions is also conducted to confirm which pyrazines are present.

Pyrazine, 2-methylpyrazine, 2,6-dimethylpyrazine, 2-ethylpyrazine, 2,3,5-trimethylpyrazine, 2-ethyl-3-methylpyrazine, 2-ethyl-3,5-dimethylpyrazine, and 2-ethyl-3,6-dimethylpyrazine are chosen to represent C1, C2, C3 and C4 level pyrazines in the standards. The standards are prepared by dissolving each pyrazine in water and performing serial dilutions.

The resulting tobacco-derived pyrazine mixture produced according to Example 16 above is mixed with 100 mL of water and distilled using a simple, short path distillation setup at atmospheric pressure and 100° C. Fractions 1, 2 and 3 are 24 mL, 21 mL and 34 mL, respectively. Distilled tobacco-derived pyrazine samples are collected and analyzed by UPLC in their original solvent, water. For GC/MS analysis, 5 mL of each fraction is extracted with 2 mL of dichloromethane.

The standards are used to create calibration curves for all eight pyrazines. Chromatograms for each of the tobacco-derived fractions are created. The concentration of each tobacco-derived pyrazine compound in each fraction is shown below in Table 7.

TABLE 7

Concentration (ppm) of Tobacco-Derived Pyrazines in Fraction 1, 2, and 3

| Compound | Fraction 1 | Fraction 1% of Total | Fraction 2 | Fraction 2% of Total | Fraction 3 | Fraction 3% of Total |
|---|---|---|---|---|---|---|
| Pyrazine | 60.14 | 8.85% | 10.226 | 10.3% | 1.872 | 8.47% |
| 2-methylpyrazine | 406.114 | 59.78% | 53.316 | 53.5% | 7.016 | 31.73% |
| 2,6-dimethylpyrazine | 184.86 | 27.21% | 27.0388 | 27.1% | 10.274 | 46.46% |
| 2-ethylpyrazine | 11.008 | 1.62% | 1.504 | 1.5% | 1.114 | 5.04% |
| 2,3,5-trimethylpyrazine | 12.986 | 1.91% | 5.862 | 5.9% | BQL | BQL |
| 2-ethyl-3-methylpyrazine | 1.56 | 0.23% | 0.532 | 0.5% | 0.896 | 4.05% |
| 2-ethyl-3,5-dimethylpyrazine | 1.936 | 0.28% | 1.194 | 1.2% | 0.94 | 4.25% |
| 2-ethyl-3,6-dimethylpyrazine | 0.75 | 0.11% | 0.0 | 0.0% | 0.0 | 0.00% |
| Total | 679.354 | | 99.6728 | | 22.112 | |

The first fraction had much higher concentrations of pyrazines compared to the second and third fractions. However, when comparing the amount of each pyrazine as a percent of the total concentration, the fractions are comparable to each other. The most abundant groups of pyrazines are C1 and C2 pyrazines. These include pyrazine, 2-methylpyrazine, 2,6-dimethylpyrazine and 2-ethylpyrazine.

The tobacco-derived pyrazine fractions are also evaluated using GC/MS for identifiable compounds with a quality match of 80 or higher with the Wiley $9^{th}$ library of mass spectra. Any peaks also present in the solvent blank are removed. The remaining clearly present and identifiable pyrazine compounds are pyrazine, 2-methylpyrazine, 2,5-dimethylpyrazine, 2,6-dimethylpyrazine, 2-ethylpyrazine, 2,3-dimethylpyrazine, 2-ethyl-6-methylpyrazine, 2-ethyl-5-methylpyrazine, vinylpyrazine, 2-ethyl-3,6-dimethylpyrazine, 2-ethyl-3,5-dimethylpyrazine, 2-methyl-6-vinylpyrazine, 2,6-diethyl-3-methylpyrazine, 2-isoamylpyrazine, 2-isoamyl-6-methylpyrazine, and 2-phenylethylpyrazine. Other compounds present and identifiable include 1,2-ditert-butylbenzene, benzaldehyde, furfuryl alcohol, nicotine, 7-azaindolizine, nicotyrine, and indole.

Example 18

Various pyrazines are synthesized via reaction of high fructose tobacco syrup, ammonium hydroxide and amino acids at 110° C. for 2 hours. Different methods of sample cleanup such as liquid-liquid extraction, liquid-solid extraction, and distillation are utilized to isolate several pyrazines from the reaction mixture.

It is demonstrated that liquid-liquid extraction of pyrazines using either hexane, MTBE, or ethyl acetate requires multiple extraction steps with fresh solvent each time. When hexane is used as the extraction solvent, no imidazole is removed with the pyrazines. However, when MTBE or ethyl acetate is employed, 4-methyl imidazole is co-extracted and further cleanup is required.

In a separate series of experiments, it is shown that bare silica can easily remove most of any unwanted material such as 4-methyl imidazole from the raffinate by passing it through the silica. A mixture of 90/10 hexane/ethyl acetate provides not only pyrazines, but also it is possible to separate C3-05 branched pyrazines from C1-C3 pyrazines.

Distillation is also used for isolation of pyrazines. Analysis of the distillate from a 300 mL reaction shows the presence of only pyrazines in a dichloromethane (DCM) extract. Also, it is important to remove residual water from the distillate. Different methods are used for this purpose. Experimental results show that a column packed with C18-bonded silica can easily remove water and, at the same time, concentrate pyrazines in a "friendly" solvent such as ethanol.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of forming pyrazines from reactants derived from a plant of the *Nicotiana* species, comprising:
   receiving a tobacco material comprising at least one of a stalk material and a root material of a harvested plant of the *Nicotiana* species;
   delignifying the tobacco material to form a tobacco-derived pulp, wherein the step of delignifying the tobacco material comprises mechanical pulping of the tobacco material to form a tobacco-derived pulp, and wherein the tobacco material has a moisture content of less than about 15% when it undergoes mechanical pulping;
   hydrolyzing the tobacco-derived pulp to form a hydrolyzed tobacco product comprising residual solids and a liquid comprising at least one tobacco-derived cellulosic sugar;
   separating the liquid comprising the at least one tobacco-derived cellulosic sugar from the residual solids;
   receiving a protein-enriched material from a plant of the *Nicotiana* species or portion thereof;
   hydrolyzing the protein-enriched material to produce a hydrolyzed product comprising at least one tobacco-derived nitrogen source;
   forming a reactant solution comprising the at least one tobacco-derived cellulosic sugar and the at least one tobacco-derived nitrogen source;
   heating the reactant solution to a reactant temperature and holding the reactant solution at the reactant temperature for a time sufficient to produce a reactant product comprising at least one tobacco-derived pyrazine; and
   isolating the at least one tobacco-derived pyrazine from the reactant product.

2. The method of claim 1, wherein the tobacco material comprises at least about 90 percent by dry weight of at least one of the stalk material and the root material of the harvested plant of the *Nicotiana* species.

3. The method of claim 1, wherein the step of hydrolyzing the tobacco-derived pulp comprises enzymatic saccharification of the tobacco-derived pulp in the presence of at least one enzyme.

4. The method of claim 1, further comprising evaporating at least a portion of the liquid comprising the at least one tobacco-derived cellulosic sugar to form a condensed syrup.

5. The method of claim 4, wherein the condensed syrup comprises at least about 80% by weight glucose.

6. The method of claim 5, further comprising isomerizing the glucose to produce high fructose tobacco syrup using glucose isomerase.

7. The method of claim 1, further comprising:
   receiving a plant material of the *Nicotiana* species;
   contacting the plant material with a solvent for a time and under conditions sufficient to extract one or more proteins from the plant material into the solvent and form a liquid protein-containing extract;
   separating a solid extracted plant material from the liquid protein-containing extract;
   clarifying the liquid protein-containing extract to form a clarified protein-containing extract and a solids fraction; and
   treating the clarified protein-containing extract so as to provide the protein-enriched material comprising at least about 60% protein by dry weight.

8. The method of claim 7, wherein the treating step comprises adjusting the pH of the clarified protein-containing extract to a pH of less than about 6 to form an acidic extract;
   isolating a precipitate from the acidic extract; and
   washing the precipitate to provide the protein-enriched material.

9. The method of claim 8, wherein the pH of the clarified protein-containing extract is adjusted to a pH of between about 4.5 to about 6 to provide a RuBisCO-containing protein-enriched material.

10. The method of claim 1, wherein the step of hydrolyzing the protein-enriched material comprises enzymatic hydrolysis of the protein-enriched material in the presence of at least one enzyme.

11. The method of claim 1, further comprising adding tobacco-derived ammonium ions to the reactant solution.

12. The method of claim 11, further comprising electrochemically reducing tobacco-derived potassium nitrate crystals to form the tobacco-derived ammonium ions in the form of ammonium hydroxide.

13. The method of claim 12, further comprising:
   receiving a tobacco biomass comprising a harvested plant of the *Nicotiana* species;
   extracting the tobacco biomass in about a 10:1 to about a 1:10 ratio of water to tobacco biomass at an elevated temperature to form a tobacco extract and fibrous tobacco solids;

separating the tobacco extract from the fibrous tobacco solids;

filtering the separated tobacco extract to form a filtered extract;

concentrating the filtered extract to form a concentrated extract;

cooling the concentrated extract to a temperature of about −5° C. to about 5° C. for about 12 hours or longer to generate the tobacco-derived potassium nitrate crystals and a residual mother liquid.

14. The method of claim 13, further comprising separating the tobacco-derived potassium nitrate crystals and the residual mother liquid, and re-cooling the residual mother liquid to a temperature of about −5° C. to about 5° C. for about 12 hours or longer to generate a second batch of the tobacco-derived potassium nitrate crystals and residual mother liquid.

15. The method of claim 13, further comprising:

separating the tobacco-derived potassium nitrate crystals and the residual mother liquid;

dissolving the tobacco-derived potassium nitrate crystals in water;

filtering the dissolved tobacco-derived potassium nitrate crystals to remove tobacco solids and form a second filtered tobacco extract;

concentrating the second filtered tobacco extract to form a second concentrated extract;

cooling the second concentrated extract to a temperature of about −5° C. to about 5° C. for about 12 hours or longer to generate purified tobacco-derived potassium nitrate crystals and a purified residual mother liquid.

16. The method of claim 1, wherein the step of isolating the at least one tobacco-derived pyrazine from the reactant product comprises at least one of liquid-liquid extraction of the reactant product, liquid-solid extraction of the reactant product, and simple distillation of the reactant product.

17. The method of claim 1, further comprising incorporating the at least one tobacco-derived pyrazine into a tobacco product.

18. The method of claim 17, wherein the tobacco product is a smoking article.

19. The method of claim 1, wherein the at least one tobacco-derived pyrazine is selected from the group consisting of pyrazine, 2-methylpyrazine, 2,5-dimethylpyrazine, 2,6-dimethylpyrazine, 2-ethylpyrazine, 2,3-dimethylpyrazine, 2,3,5-trimethylpyrazine, 2-ethyl-6-methylpyrazine, 2-ethyl-5-methylpyrazine, 2-ethyl-3-methylpyrazine, vinylpyrazine, 2-ethyl-3,6-dimethylpyrazine, 2-ethyl-3,5-dimethylpyrazine, 2-methyl-6-vinylpyrazine, 2,6-diethyl-3-methylpyrazine, 2-isoamylpyrazine, 2-isoamyl-6-methylpyrazine, 2-phenylethylpyrazine, and combinations thereof.

20. The method of claim 1, wherein the step of delignifying the tobacco material excludes a bleaching operation.

* * * * *